United States Patent
Jain et al.

(10) Patent No.: US 11,482,335 B2
(45) Date of Patent: Oct. 25, 2022

(54) SYSTEMS AND METHODS FOR PREDICTING PATIENT OUTCOME TO CANCER THERAPY

(71) Applicant: DHRISTI INC., Saratoga, CA (US)

(72) Inventors: Parag Jain, Palo Alto, CA (US); Rajat Roy, Saratoga, CA (US); Bijay Shankar Jaiswal, San Mateo, CA (US)

(73) Assignee: PATHOMIQ INC., Saratoga, CA (US)

( * ) Notice: Subject to any disclaimer, the term of this patent is extended or adjusted under 35 U.S.C. 154(b) by 337 days.

(21) Appl. No.: 16/718,549

(22) Filed: Dec. 18, 2019

(65) Prior Publication Data

US 2021/0193323 A1    Jun. 24, 2021

(51) Int. Cl.
  *G16H 50/30*    (2018.01)
  *G16H 50/20*    (2018.01)
  *G16H 30/40*    (2018.01)

(52) U.S. Cl.
  CPC .......... *G16H 50/30* (2018.01); *G16H 30/40* (2018.01); *G16H 50/20* (2018.01)

(58) Field of Classification Search
  None
  See application file for complete search history.

(56) References Cited

U.S. PATENT DOCUMENTS

| | | |
|---|---|---|
| 2008/0082468 A1 | 4/2008 | Long |
| 2009/0035766 A1 | 2/2009 | Khan et al. |
| 2011/0119212 A1* | 5/2011 | De Bruin ............... G16H 50/70 706/12 |
| 2013/0290006 A1* | 10/2013 | Kamath ................. G16H 50/20 705/2 |
| 2014/0193062 A1 | 7/2014 | Zhukov et al. |
| 2014/0314286 A1 | 10/2014 | Madabhushi et al. |
| 2016/0253466 A1* | 9/2016 | Agaian .................. G06K 9/629 382/128 |
| 2017/0270666 A1* | 9/2017 | Barnes ...................... G06T 7/12 |
| 2019/0286936 A1* | 9/2019 | Fuchs .................... G16H 30/40 |
| 2021/0118136 A1* | 4/2021 | Hassan-Shafique ... G16H 10/60 |

FOREIGN PATENT DOCUMENTS

WO    WO-2020069501 A1 *    4/2020    ........... G06T 7/0012

OTHER PUBLICATIONS

Daisuke Komura, Shumpei Ishikawa, Machine Learning Methods for Histopathological Image Analysis, Computational and Structural Biotechnology Journal, vol. 16,2018, pp. 34-42, ISSN 2001-0370, https://doi.org/10.1016/j.csbj.2018.01.001. (Year: 2018).*

(Continued)

*Primary Examiner* — Devin C Hein
(74) *Attorney, Agent, or Firm* — Cognition IP, P.C.; Edward Steakley; Saleh Kaihani

(57) ABSTRACT

Disclosed are systems and methods for predicting patient response to a treatment option. In one embodiment, the image slides from patient tissue samples are divided into patches and morphological patterns correlated with a disease outcome are labeled and given a patch-level score, based on whether the morphological patterns occur only in patients with good outcomes or patients with poor outcomes. A patient-level score can be generated based, at least partly, on the patch-level scores. Patch-level scores can identify regions of interest for targeted biomarker identification.

20 Claims, 11 Drawing Sheets

(56) References Cited

OTHER PUBLICATIONS

International Search Report and Written Opinion in International Application No. PCT/US2019/067114, dated Feb. 26, 2020.

Datto et al., "Artificial Intelligence in Predicting Bladder Cancer Outcome: A Comparison of Neuro-Fuzzy Modeling and Artificial Neural Networks," Clinical Cancer Research, vol. 9, Sep. 15, 2003, pp. 4172-4177. Retrieved on Feb. 6, 2020 <https://clincancerres.aacrjournals.org/content/9/11/4172>.

Yue et al., "Colorectal Cancer Outcome Prediction from H&E Whole Slide Images using Machine Learning and Automatically Inferred Phenotype Profiles," School of Computer Science & School of Medicine, University of St Andrews, UK, arXiv:1902.03582v2 [eess.IV], Mar. 9, 2019. <https://arxiv.org/pdf/1902.03582.pdf>.

\* cited by examiner

SYSTEMS AND METHODS FOR PREDICTING PATIENT OUTCOME TO CANCER THERAPY

BACKGROUND

Field

This invention relates generally to the field of disease detection and treatment identification, and in particular to using artificial intelligence in predicting patient outcome to cancer therapy.

Description of the Related Art

Current methods of developing treatment options or administering those treatment options for complex diseases, such as cancer, include observing a patient's response to treatment, based on the stage of the disease in the patient. Oncologists however are unable to identify which patient will fail Standard-of-Care therapy early on and could benefit from advanced/experimental therapy at an early stage. Pharmaceutical companies are running clinical trials to get advanced therapy to patients, but most trials fail to attain statistical significance as patients are randomly selected not knowing the likely responders. Even when clinical trials are successful and drugs get approved, only a small percentage of patients respond to that drug in the clinic. Systems and methods that can identify responders vs non-responders to cancer therapy with higher accuracy are warranted to select the right treatment for individual patient at the right disease state.

Current techniques to discover biomarkers that predict patient response are focused on structured molecular data, such as genomic and proteomic data. The molecular analysis is done at a whole tissue level which delivers an average molecular signature across 10s of 1000s of cancer, benign and micro-environmental (stroma, immune etc.) cells. This technique works when a single or few genes are heavily over-expressed in cancer and/or its micro-environment. However, tumors are inherently heterogeneous and there are several molecular subtypes with varying levels of expression in a tissue sample. In many cases, <1% of the cancer cells may be the most aggressive and informative of molecular pathways of the disease and of the patient outcome. This molecular signal gets lost when averaged over the entire tissue.

Also, tumor alone does not capture the full picture—it is the spatial interaction of the tumor with the Tumor Micro-Environment (TME) that includes stroma, several types of immune cells, blood vessels etc. whose interplay determines tumor aggressiveness and patient response to a particular therapy. Current proteogenomic analysis is not able to capture the TME dynamics, nor is there one single RNA or protein that is driving patient response and outcome.

Furthermore, a source of hinderance in predicting patient outcome is that existing technology does not provide a convenient and efficient tool to process the sheer volume of the data collected from each patient these days that needs to be processed for patient outcome prediction. For instance, histopathology is the cornerstone of cancer diagnosis, and a lot of molecular changes and TME elements result in morphological changes that are visible on the tissue slides. Examining patient tissue samples obtained by histopathology (e.g., Hematoxylin & Eosin or H&E slides) is the current clinical practice to diagnose and stage cancer and other diseases and in some cases is used to prognosticate patient outcome for diseases such as prostate and gastrointestinal tumors. The process calls upon the experience of human pathologists to interpret the vast amount of data present in a cancer and its surrounding normal tissue architecture that could be seen in an H&E stained slide. These professionals rely, in part, on identification of known morphological patterns on the H&E slides or other sample patient image data to arrive at a diagnosis and staging of disease. However, as the described embodiments will illustrate, there are several other novel patterns and morphometric features that can be extracted using AI and deep learning from these tissue slides that are unknown in terms of predictive significance and are therefore not used to prognosticate patient outcome.

While biochemical and molecular analysis can yield important insights into the mechanisms of therapy response and disease pathways that can enable more accurate prediction, current methods do not provide a targeted region, or a spatial-temporal protein expression/localization for those analysis. The current practice of biochemical, molecular and pathway analysis on a whole sample tissue slide loses many predictive markers for disease/therapy outcome.

Consequently, there is a need for computer aided systems and methods that can discover, cluster and extract novel morphometric features that correlate with patient outcome from histopathology slides in an unsupervised manner. The methods also need to identify specific Regions of Interest (ROIs) on the tissue slides that are most predictive and does molecular analysis on the ROIs to discover novel biomarkers that predict patient response and integrate to the platform to further improves predictive response.

Furthermore, there is a need for computer systems and methods that can isolate, identify, enumerate and quantitate different types of cells and the proteins and/or biomarkers present in the tumor and its microenvironment that is predictive of patient outcome or response that can be subjected to targeted biochemical and molecular analysis.

SUMMARY

In one aspect, a method of predicting patient response to therapy is disclosed. The method includes steps of: receiving a plurality of patient tissue image slides; receiving a plurality of patient outcome data; dividing the image slides into patches; receiving a plurality of labels correlated with a disease or lack thereof, wherein each label comprises of a morphological type; converting each patch to a patch vector; training an artificial intelligence network, based on the plurality of labels to identify the morphological types associated with each label in the image slides; generating labeled patch vectors, wherein the label of a patch vector is assigned based, at least partly, on the plurality of the labels and the morphological type expressed in the patch; clustering the labeled patch vectors, with an unsupervised artificial intelligence network, wherein each cluster corresponds to a morphological subtype expressed in the patch corresponding to the labeled patch vector and a patient outcome; generating a patch-level score for each patch based at least partly on the cluster to which the patch vector of the patch belongs; and generating a patient-level score for each patient, at least partly based on the patch-level scores generated for each patient.

In one embodiment, generating the patch-level score further includes: converting regions surrounding each patch to microenvironment vectors; obtaining mean vectors by averaging the patch vectors corresponding to the patches with the microenvironment vectors; clustering the mean vectors; sampling input mean vectors from each cluster; and using an artificial intelligence model, comprising a plurality of weights, convert each sampled input mean vectors to a patch-level score.

In another embodiment, the method further includes selecting a first group of patches having highest patch-level scores amongst the patch-level scores; selecting a second group of patches having lowest patch-level scores amongst the path-level scores; combining the first and second groups; and generating the patient-level score.

In some embodiments, the method further includes comparing the patient-level score for a patient to the patient outcome data; and if the patient-level score does not align with the patient outcome data modify the weights of the artificial intelligence model.

In one embodiment, the method further includes identifying regions of interest in the patient image slide, at least partly based on the patch-level scores, wherein the regions of interest comprise biomarkers predictive of patient outcome.

In another embodiment, the method further includes performing molecular analysis on the regions of interest; and identifying biomarkers based at least partly on differential expressions of biological macromolecules, comprising DNA, RNA or proteins, on the regions of interest versus other regions of the patient tissue image slide, wherein the biomarkers are over or under expressed in the regions of interest versus other regions.

In one embodiment, the method of further includes generating a biomarker slide based on the identified biomarkers; generating a patient image slide annotated with the regions of interest; and co-registering the biomarker slide and the annotated patient tissue image slide.

In some embodiments, generating labeled patch vectors further includes receiving a plurality of auxiliary labels; and when an auxiliary label is applicable to a patch vector or its corresponding patch, determine the label of the patch by processing the patch through the artificial intelligence network at a plurality of distinct sizes and/or resolutions.

In another embodiment, the method further includes clustering the input training data of the artificial intelligence network based, at least partly, on the output vectors of the artificial intelligence network, wherein the output vectors of the artificial intelligence network indicate an underlying morphological pattern in the patient image slide; and sampling uniformly across the clusters of the input training data in subsequent training passes of the artificial intelligence network.

In one embodiment, the method further includes assigning labels to patch vectors based, at least partly, on a confidence level; determining label assignments having a low confidence level; determining input patch vectors generating the low confidence level assignments; and sampling input training data of the artificial intelligence network to include a pre-determined percentage of input training data from the input patch vectors having generated low confidence level assignments in previous training passes of the artificial intelligence network.

In another aspect a system of predicting patient response to therapy is disclosed. The system includes a patch generator configured to receive a plurality of patient tissue image slides and divide the image slides into patches; a disease detection and grading module, comprising an artificial intelligence network, wherein the disease detection and grading module is configured to: receive patient outcome data; receive a plurality of labels correlated with a disease or lack thereof, wherein each label comprises a morphological type; covert each patch to a patch vector; train the artificial intelligence network, based on the plurality of labels to identify the morphological types associated with each label in the image slides; generate labeled patch vectors, wherein the label of a patch vector is assigned based, at least partly, on the plurality of the labels and the morphological type expressed in the patch; a morphology detector comprising an unsupervised machine learning model configured to cluster the labeled patch vectors, wherein each cluster corresponds to a morphological subtype expressed in the patch corresponding to the labeled patch vector and a patient outcome; and a region of interest and outcome prediction module configured to: receive the clustered labeled vectors and generate a patch-level score for each patch based at least partly on the cluster to which the patch vector of the patch belongs; and generate a patient-level score for each patient, at least partly based on the patch-level scores generated for each patient.

In one embodiment, generating the patch-level score further includes converting regions surrounding each patch to microenvironment vectors; obtaining mean vectors by averaging the patch vectors corresponding to the patches with the microenvironment vectors; clustering the mean vectors; sampling input mean vectors from each cluster; and using an artificial intelligence model, comprising a plurality of weights, convert each sampled input mean vectors to a patch-level score.

In another embodiment, the region of interest and outcome prediction module is further configured to perform steps, including: selecting a first group of patches having highest patch-level scores amongst the patch-level scores; selecting a second group of patches having lowest patch-level scores amongst the path-level scores; combining the first and second groups; and generating the patient-level score.

In one embodiment, the region of interest and outcome prediction module is further configured to perform steps, including: comparing the patient-level score for a patient to the patient outcome data; and if the patient-level score does not align with the patient outcome data modify the weights of the artificial intelligence model.

In some embodiments, the region of interest and outcome prediction module is further configured to identify regions of interest in the patient tissue image slide, at least partly based on the patch-level scores, wherein the regions of interest comprise biomarkers predictive of patient outcome.

In another embodiment, the system further includes a spatial profiling and biomarker identification module configured to: perform molecular analysis on the regions of interest; and identify biomarkers based at least partly on differential expressions of one or of DNA, RNA or proteins on the regions of interest versus other regions of the patient tissue image slide, wherein the biomarkers are over- or under-expressed in the regions of interest versus other regions, wherein molecular analysis reveals biologically discrete subsets and pathways and mechanism-related response and outcome.

In another embodiment, the system further includes a co-registration module configured to: generate a biomarker slide based on the identified biomarkers; generate a patient tissue image slide annotated with the regions of interest; and superimpose the biomarker slide and the annotated patient tissue image slide.

In another embodiment, the disease detection and grading module is further configured to generate labeled patch vectors by: receiving a plurality of auxiliary labels; and when an auxiliary label is applicable to a patch vector or its corresponding patch, determine the label of the patch by processing the patch through the artificial intelligence network at a plurality of distinct sizes and/or resolutions.

In some embodiments, the disease detection and grading module is further configured to: cluster the input training data of the artificial intelligence network based, at least partly, on the output vectors of the artificial intelligence network, wherein the output vectors of the artificial intelligence network indicate an underlying morphological pattern in the patient image slide; and sample uniformly across the clusters of the input training data in subsequent training passes of the artificial intelligence network.

In one embodiment, the disease detection and grading module is further configured to: assign labels to patch vectors based, at least partly, on a confidence level; determine label assignments having a low confidence level; determine input patch vectors generating the low confidence level assignments; and sample input training data of the artificial intelligence network to include a pre-determined percentage of input training data from the input patch vectors having generated low confidence level assignments in previous training passes of the artificial intelligence network.

BRIEF DESCRIPTION OF THE DRAWINGS

These drawings and the associated description herein are provided to illustrate specific embodiments of the invention and are not intended to be limiting.

DETAILED DESCRIPTION

The following detailed description of certain embodiments presents various descriptions of specific embodiments of the invention. However, the invention can be embodied in a multitude of different ways as defined and covered by the claims.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

When the terms "one", "a" or "an" are used in the disclosure, they mean "at least one" or "one or more", unless otherwise indicated.

Figure 1:
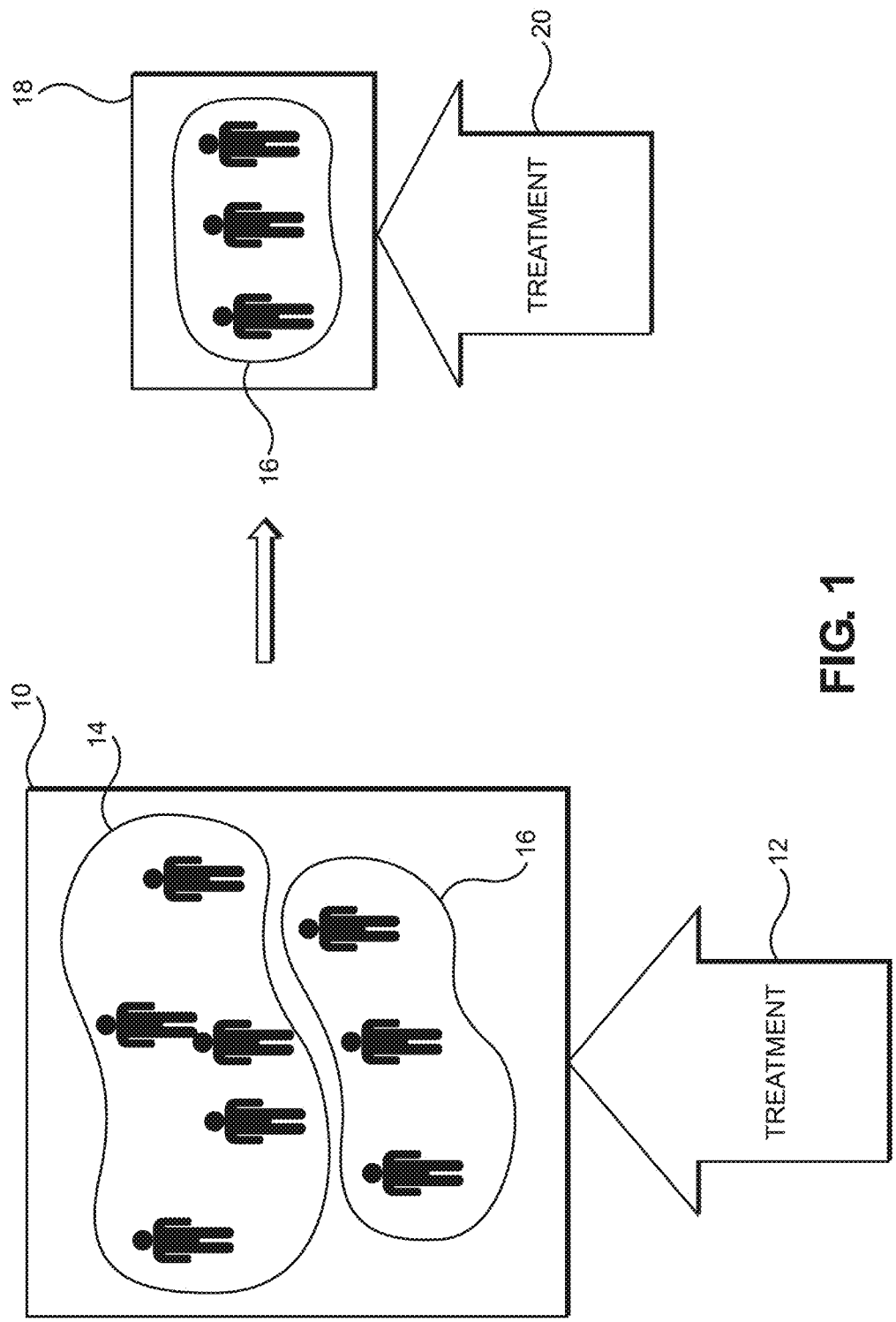
FIG. 1 illustrates an example of disease progression stages in relation to available treatment options.

In the context of disease treatment, current medical practice and standard-of-care (SOC) might treat patients based on stages of a disease and the patient's responsiveness to available treatments for those stages. These treatments in case of cancer may include administrating drugs, radiation therapy, surgery or other forms of treatment. If the patient does not respond to available treatments for the stage of disease the patient is in, the patient transitions to a different stage, where different, and potentially more aggressive treatment options may be applied. Later stage treatment options may include experimental or advanced therapy options. FIG. 1 illustrates an example of disease progression stages in relation to available treatment options. In the first disease stage 10, treatment options 12 are applied. A first group of patients 14 respond well to the treatment options 12. A second group of patients 16 do not respond well to the treatment options 12 and their disease progresses to the disease stage 18. Treatment options 20 are available and may be applied for the second group patients 16 in the disease stage 18.

The dynamics of disease progression and applied treatment, in some cases, are as follows. Most patients in earlier stages, respond well to treatment, but a smaller percentage of patients in earlier stages do not respond well to the treatment options applied in those earlier stages. For example, the first group of patients 14 that respond well to treatment options 12 can be a substantially larger number than the second patient group 16 that do not respond well to the treatment options 12. Furthermore, the treatment options that are available to be applied in the later stages can have more efficacy if they are applied in earlier stages. In other words, for the second patient group 16, if treatment options 20, were applied, when those patients were in an earlier disease stage 10, the treatment options 20 may have had more efficacy.

Furthermore, later stage treatment options 20 can include potentially more aggressive treatments or experimental advance therapy options. In some cases, the late stage treatment options 20 can be experimental in nature and can include treatment options that governmental approval may not yet have been obtained. Nonetheless, the second group patients 16 may substantially benefit from those treatments if they were applied in an earlier disease stage 10. Consequently, in terms of disease treatment efficacy and treatment discovery, systems and methods that help early identification of patients that respond well to available treatment options can be beneficial and needed.

Also, pharmaceutical companies are running several thousand clinical trials to get advanced and novel drugs to market across several cancer indications. Lack of reliable predictive biomarkers to identify responders vs non-responders to these drugs result in random selection of patients for the trials and contributes to the low success rate. Even when some of these trials succeed, only a small percentage of patients respond to the drugs when administered in clinical practice. Consequently, there is a huge unmet need for pharmaceutical companies to identify responders to a new drug early on.

Biochemical signatures, biomarkers etc. can be used to predict patient outcome. Some genomics and proteomics techniques to discover biomarkers that predict patient response are focused on biochemical markers and the structured molecular data of those biochemical markers, such as DNA, RNA, and protein data. This approach has major challenges. First, molecular analysis is done from DNA, RNA, and protein extracted from whole tissue which delivers an average molecular signature across tens of thousands of cancer, benign and micro-environmental (e.g., stroma, immune etc.) cells. Consequently, this approach works better when a single or few genes are heavily overexpressed or under-expressed across an entire tissue. However, tumors can be inherently heterogeneous, and there are several molecular subtypes with varying levels of aggressiveness that show up in the same tumor and the tumor micro-environment. This molecular signal gets lost when averaged over an entire tissue.

Second, biochemical, molecular, structural or other analysis of tumor alone do not present a full picture of the disease. In many cases, it is the spatial interaction of the tumor with the tumor micro-environment (TME), including the stroma, several types of immune cells, blood vessels etc., whose interplay determines patient response. Many current genomic analyses are not able to capture the TME dynamics, nor is there one single RNA or protein that can be linked to driving patient response. Nevertheless, Histopathology remains the cornerstone of cancer diagnosis. Many molecular changes and TME elements that are linked to disease can result in morphological changes that are visible on tissue slides. Consequently, systems and methods that can identify and extract morphometric features that correlate with patient outcome from histopathology slides are valuable in disease treatment. Therefore, it is advantageous to employ artificial intelligence (AI) in an unsupervised manner to identify and extract these morphologic features.

Furthermore, the field of studying biomarkers and identification of morphologic features for drug and treatment discovery can be slowed down by the sheer number of samples and patient data that need to be analyzed to identify biomarkers of interest. For example, some methods rely on or work in conjunction with laboratory test results. Described embodiments substantially reduce the volume and number of data that need to be analyzed in a laboratory environment, making the applications of the described embodiments more practical than existing systems. For example, the described embodiments can identify regions of interest (ROIs) on tissue slides that are more predictive, and more promising or relevant for performing laboratory molecular analysis to identify predictive biomarkers of patient response. The identification of aberrant genes/proteins present in the ROI known to be involved in therapy response prediction may also enhance easy detection of disease or therapy response biomarkers, unlike techniques which operate on the whole tissue slide, where the abnormality could be masked by the large preponderance of cells with normal proteogenomic patterns.

Current methods of cancer diagnosis, and in some cases cancer prognosis using histopathology include trained pathologists examining sample slides from a patient. The pathologists examine patient cells and look for patterns and other markers as identified in one or more SOC trade guidelines, such as guidelines published by the national comprehensive cancer network (NCCN). Pathologists identify type of cells, they are observing in the sample, as well as identifying whether a patient sample contains benign or malignant tumor cells, and in some cases, a grading of the detected cancer cells. The SOC guidelines are typically generated by researchers and health care professionals who through their years of experience observing patient samples have accumulated a knowledge-base of correlations between features in patient sample tissue and cases of other patients in the past and an associated outcome with the observed features or combination of several specific features. In this paradigm, the identification of biomarkers is limited to the guidelines and past experiences of the healthcare professionals. The process of updating the guidelines and the way the pathologists scan, examine and identify biomarkers is therefore a dynamic and at the same time a slow process.

In other words, the current methodologies of biomarker identification can include matching features from a sample space against a limited-scope database of known biomarkers. The described embodiments, on the other hand, can utilize unsupervised artificial intelligence architectures to scan tissue sample image data at a much faster speed and also identify biomarkers predictive of patient outcome that has never been previously identified.

Another challenge with traditional methods of identification of biomarkers and drug target is that diseases, such as cancer can be highly heterogenous and evolving over time. One tumor may include many different molecular subtypes some of which may be biomarkers predictive of patient response. Many techniques look at a small subset of potential molecular subtypes by analyzing a whole tissue slide from a patient. That approach has identified some useful biomarkers, but a wealth of data and information in each patient slide also remains unexamined. As a result, many patients still get baseline treatments, even though they may be good candidates for a different treatment option. Not knowing the relevant biomarkers, the success rate of many treatments is lower than maximum because a large patient population are treated with the same treatment options, without regards to the anticipated response. What is worse, is that in the absence of better alternative, low-success rate treatment options become SOC. Systems and methods that can identify biomarkers predictive of patient response will help to identify patients, who are good candidates for a specific treatment option and deliver targeted and personalized therapies to an individual patient.

Furthermore, patient outcome and responsiveness can be a multimodal problem, where tumor alone or normal disease pathways and mechanisms may not be the only relevant factors. For example, a tumor micro-environment (TME) can play a significant role in patient responsiveness. A drug can be correctly designed based on a disease or tumor, but it might not reach the correct target in the patient if the drug is not designed with the TME of the tumor cells in mind. As an example, a drug might be correctly designed to activate immune system, but in some patients, the tumor might have few infiltrated immune cells, or might have immune suppressor cells nullifying the drug effect. The described embodiments use, the TME of a cell, including stroma, immune cells, blood vessels etc., as well as the tumor cells, when identifying biomarkers, thus enabling the selection of treatment options with higher success potential.

In one sense, the traditional methods of biomarker identification have relied on molecular biologists and pathologists as the initial actors that identified the biomarkers. The results of human-driven identification of biomarkers predictive of patient response were then verified using bioinformatics and statistical analysis. As discussed earlier, the human-driven method of biomarker identification is necessarily limited in the size and number of patient samples capable of being analyzed in laboratory settings, and by the patterns and structures that have previously been identified in research and trade guidelines. The disclosed embodiments, on the other hand, analyze tissue samples in a patient or patient population and identify biomarkers predictive of patient response that may not have been previously known. The results, including the newly identified biomarkers, can be further confirmed by pathologists or biologists in a laboratory setting.

For pharma and oncologists, each stage and sub-type of disease and each potential drug is a unique challenge for biomarker discovery and drug development. The disclosed computer aided systems and methods that correlate disease outcome with tissue morphology are agnostic to the type of cancer and of its treatment. The systems and methods rank morphological features based on known patient outcome to a particular drug to treat a specific disease but do not depend upon the drug mechanism itself. They can therefore be applied to any disease such as cancer that changes morphology and the treatment of interest.

In another embodiment, the method can also be used to identify morphometric features on patient tissues that correlate with a particular molecular change, such as protein loss or gene mutations without the need for a molecular test such as immunohistochemistry (IHC) or gene panel testing. It can rank the morphological features in an unsupervised manner using only the molecular status as label and determine the lead morphology features that can be related to the molecular change.

Figure 2:
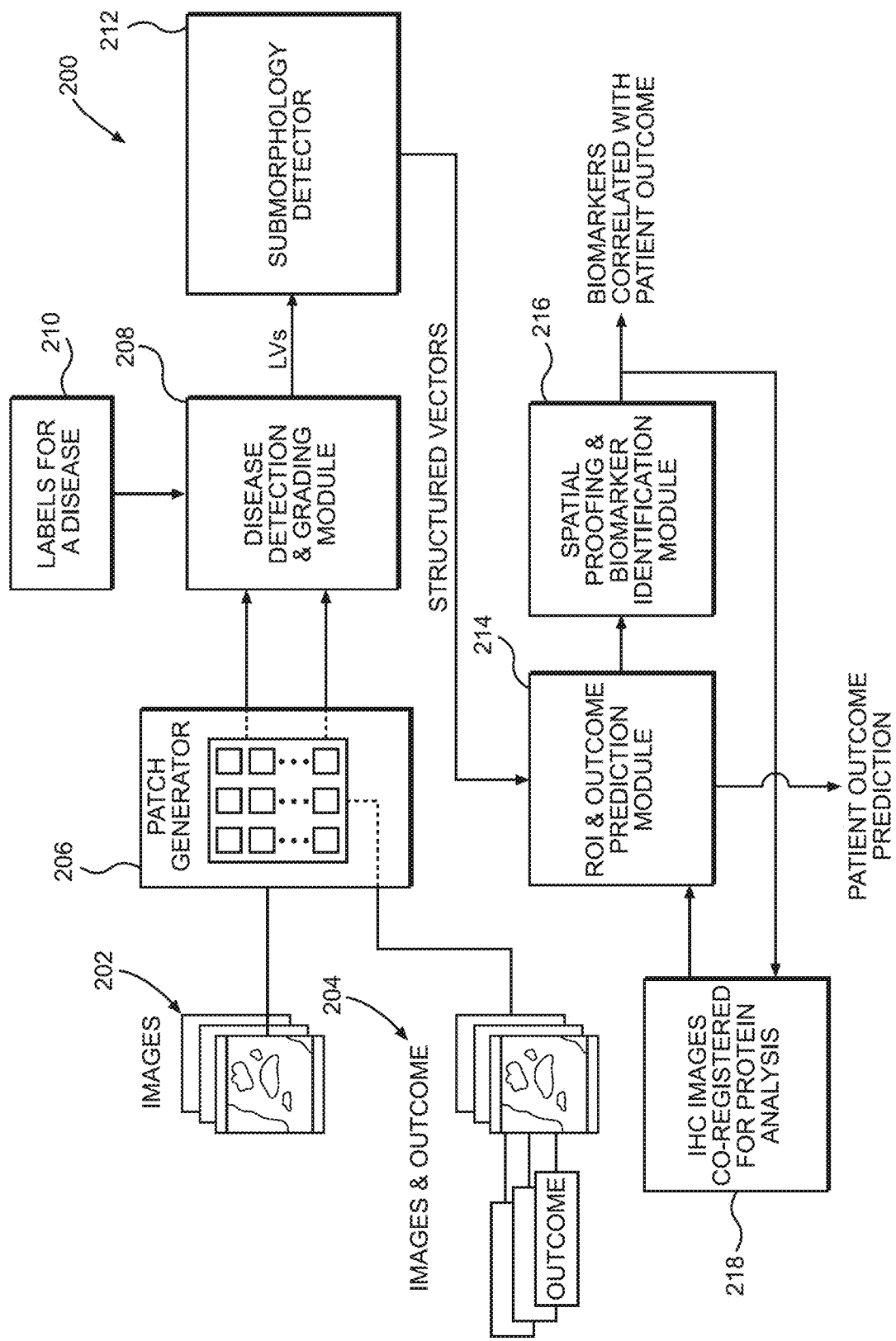
FIG. 2 illustrates a patient outcome prediction system according to an embodiment.

FIG. 2 illustrates a patient outcome prediction system 200 according to an embodiment. Images 202 containing patient data can be input to the system. Images 202 may be the whole slide images (WSI) of patient tissue sample stained with Hematoxylin & Eosin (H&E) at various magnifications, including but not limited to 10×, 20×, 40×, etc. In other embodiments, any image containing patient data, such as X-Ray or IHC images can be input to the system. Some images 204 can include an indication of patient outcome with them. For example, for every image 204, a meta data in the image file or some other form of data-association can indicate whether the patient successfully responded to a treatment or whether the patient did not respond well to a treatment, or other patient outcome data. A patch generator module 206 disclosed here can divide the images into tiles or patches. The sizes of the patches can depend on the implementation and the size of the original images 202 or 204. As an example, the image (shown in FIG. 4 or 6) can be divided up into patches of various sizes, including but not limited to 256 by 256 or 512 by 512 pixels.

Next, a disease detection and grading module (DDGM) 208 transfers the image patches into a vector representation. The DDGM 208 can receive labels 210 for a given disease and using supervised artificial intelligence techniques can determine which label applies to a given patch and augment a vector representation of the patches with applicable labels. These labeled vectors are input to a sub-morphology detector 212, which can use unsupervised learning to determine further morphological sub-patterns within the labels 210. The sub-morphology detector 212 can output structured vectors what include vector representations of image patches labeled with labels 210 and morphological sub-patterns determined by unsupervised learning. The structured vectors outputted from sub-morphology detector 212 are input to a region of interest (ROI) and outcome prediction module 214, which can rank the patches in terms of patient disease outcome and based on whether the determined morphological sub-patterns to which a patch belongs occur in patients with adverse outcomes or patients with good outcome or response treatment. The ranking includes assigning the patches a patch-level score. The patch-level scores can be combined to arrive at a patient-level score indicative of a prediction of a patient's response to a treatment. In one embodiment, a patch-level score can be a number between 0 and 1, where a high score (approximately 1) reflects that the morphological sub-pattern detected for a patch, only shows up in patients with adverse outcome, while a low score (approximately 0) reflects that the morphological sub-pattern only shows up in patients with good outcome.

Patch-level scores can also be used to determine regions of interest on patient's tissue for which further focused laboratory, biochemical or biomarker identification analysis yields information about predicting patient response and/or fine-tuning the artificial intelligence models within the system 200 and/or the ROI and outcome prediction module 214. The regions of interest can capture data on various patient tissue, such as tumor, immune and stromal cells and as a result the ROIs can capture both tumor heterogeneity as well as tumor micro-environment (TME) elements that are prognostic or predictive of the patient outcome.

The ROIs can be input to a spatial profiling and biomarker identification module (SPBI) module 216, where molecular analysis is performed. The molecular analysis is performed on the ROIs to capture differential expression of proteins/RNA in the regions marked as ROI versus regions not marked as ROI. The correlation is done on ROI vs non-ROI of patients with adverse outcome, as well as between patients that have different outcomes to identify the protein/RNA markers that are driving the patient outcome.

In some embodiments, an IHC or immunofluorescence (IF) module 218 can be used. The IHC/IF biomarker slides can be generated for the protein markers identified by SPBI module 216 to capture the spatial distribution in the TME. These biomarker slides can be co-registered with the H&E slides (or other type of input images if used) to determine patch-level biomarker quantification and distribution, as well as other prognostic or predictive data. The combination of biomarker expression (quantity) with morphology data (morphological sub-pattern indication identified by the sub-morphology detector 212) can be used to further improve the accuracy of patient outcome prediction by various modules of system 200, including the ROI and outcome prediction module 214.

In one aspect, the system 200 reduces the complexity of data present in a patient image slide to a data structure. Images 202 and 204 can be WSI or any digitized version of patient tissue, bone or other anatomical regions included but not limited to biopsied tissue, resected samples, circulating blood cells, etc. The images can be divided to a range of 50 to 100,000 patches in some embodiments. These patches can contain different expressions of tumors, benign cells and the microenvironment of the cells. In one sense, the input to the system 200 can include a vast and complex dataset of images containing millions of cells and thousands of patches. The system 200 analyzes this complex dataset and transfers it into structured and usable data for disease and patient response prediction, in one aspect, by determining morphological similarity and determining a more limited dataset of morphological sub-patterns within which these millions of cells and thousands of patches may be classified.

The system 200 performs vectorization on the input image patches and captures morphological similarity between those patches by performing vector operations on the vectors resulting from the patches. In one respect, the tissue space observed in image slides for a given disease (e.g., a tumor type) can be broken down to distinct categories of morphological sub-patterns. For example, within a broader morphological pattern labeled by labels 210. For example, one label 210 might be cells that have morphological patterns of benign cells, while there may be 50 morphological sub-patterns of those benign cells which can further classify those benign cells with more granularity and precision. In routine clinical practice, those morphological sub-patters may be unknown or not labeled to increase the reading efficiency of human pathologists. Nonetheless, those sub-patterns can contain valuable and more targeted information to treat disease or predict patient outcome. The system 200 can determine these sub-patterns within a given label and reduce the complexity of the data.

The input images 202 may be, without any associated patient outcome and for the purpose of training the artificial intelligence networks of the system 200 to identify various morphological sub-patterns. On the other hand, input images 204 may include patient outcome data, so the system 200 can additionally identify whether the detected morphological sub-patterns occur in patients with good or adverse outcomes. In the case of cancer, patients who respond well to a treatment, express the cancer on their tissues in morphologically different ways than the patients who do not respond well to the treatment. Identification of morphological sub-patterns that occur only in patients with good outcome versus those that occur in patients with poor outcome can act as a marker or signature of the category to which a patient might be predicted to belong. Consequently, the detected morphological sub-patterns identify signatures or signals indicative of patient outcome or response, which is used to predict patient outcome or response at an earlier stage of a disease.

In another aspect, the system 200 reduces the complexity of the input data and the overall problem of identifying morphological markers predictive of patient response. For example, at the stage of dividing the input images into patches, hundreds to thousands of patches might exist per patient where thousands of patients might be participating in a treatment program or in a clinical trial. Each image has in the order of gigabytes of data per image. The system 200 reduces the complexity of the input data and the biomarker/morphological identification to, for example, tens of thousands of morphological sub-patterns, where every patient data can be expressed in terms of structured vectors including identification of detected morphological sub-patterns. Vectors can be analyzed between patients with good outcome and patients with poor outcome. Patches with high predictive value and low predictive value can be identified. For example, patches belonging to morphological sub-patters occurring only in patients with adverse outcomes (e.g., failing treatment) can be given a high score. An artificial intelligence model can be trained to rank patches and assign them scores, based on known patient outcomes. The model can learn which patches only occur in patients who fail treatment, which patches only occur in patients who respond well to treatment, and which patches occur in both groups (and are therefore of low predictive value). Accordingly, the model can assign a score to each patch vector and its corresponding vector.

In some embodiments, the disease detection and grading module 208 can be exposed to patient data in two ways. Patient Images 202 do not include patient outcome data. Patient outcome data can be difficult or time consuming to obtain. In some cases, patient outcome data can be available only after following up with a patient 3-5 years after a treatment option is administered. Nonetheless, the artificial intelligence models of the disease detection and grading module 208 can be exposed to input patient image data, without any known patient outcome, for the purpose of training the models to better identify morphological similarity and morphological patterns in patient image data. On the other hand, the disease detection and grading module 208 and the artificial intelligence models therein can be exposed to images 204, where the patient outcome is known, so the models of the system 200 can associate the detected morphological patterns and sub-patterns to a patient outcome and learn how to rank a detected morphological pattern in terms of patient outcome.

In other words, ranking of patches is specific to a particular task, which is specific to a particular clinical question, while detecting morphological similarity (detecting patterns and sub-patterns) can be universal, because a disease (such as cancer) shows up in patient tissue in so many different ways, regardless of the treatment given. Consequently, the models of disease detection and grading module 208 can be improved by exposing them to more patient images, regardless of patient outcome.

In one aspect, the supervised learning models of the system 200 are trained to identify morphological patterns associated with the labels 210 and the unsupervised learning models of the system 200 can identify morphological sub-patterns within the tissue samples labeled by supervised learning models of the system 200. Consequently, the system 200 can identify morphological similarity (morphological patterns and sub-patterns) through unsupervised networks across a population of patients for a given disease. Input images 204 that include patient outcome data can be processed to rank each patch within those images with a score indicative of patient outcome. The patch-level scores can be combined to yield a patient-level score for each patient. The patient-level score indicates a prediction of the patient response to a given treatment.

Additionally, patch-level scores yield ROIs that are candidates for more analysis, both for training the models of the system 200 and for predicting patient outcome or response. Instead of performing molecular analysis of a whole patient image slide, only the regions of an image that contain morphological patterns and sub-patterns that only occur in one group of patients, are analyzed in more detail to accurately yield biomarkers predictive of patient outcome. At the same time, the ROIs identified by the models of the system 200 include the environment and the context of cell tissues to make an improved analysis of those regions, taking into account the heterogeneous nature of cancer. The same tumor cells can look and behave differently across different regions of the tissues, because cancers and diseases are not uniformly mutating or evolving across different sites. Similarly, the microenvironments of the cells also can look different depending on where in the tissue they are from. There may be different types of immune cells, blood vessels and stromal cells that appear in the images 202 and 204 differently depending on the region of the tissue they are from. Consequently, the ranking and scoring of image patches in the system 200 can be at least partially based on the environment and the microenvironment of the cells.

As discussed earlier, the system 200 makes possible analyzing regions of interests in a tissue, as opposed to a whole slide analysis of the tissue. In other words, the system 200 narrows down the field of view to regions that have predictive value. Molecular analysis of those regions can identify the biological mechanisms and pathways that are driving a detected phenotype (morphological pattern or sub-pattern). In other words, the visible regions on patient image slide (such as an H&E image slide) is a manifestation of a tumor, but there are biochemical changes within those cells captured by the image slide that constitutes the basis for the manifestation or morphological patterns or sub-patterns that have appeared in a patient image slide. Identification of those biological processes and pathways through molecular analysis allows for accurate identification of predictive biomarkers as well as developing drugs and treatment options that target those pathways and/or explain why patients respond or do not respond to a given treatment. Many different techniques can be used for further analysis of the ROIs in detail. These can include IHC imaging, IF imaging, genetic profiling and other techniques. These techniques can identify tumor cells, immune cells or other cellular and subcellular components and molecules in the ROIs and mutations or evolutions in those cells. Such identifications can be used for further refinement of the predictive models of the system 200 and/or for better understanding of the disease or patient outcome response to a given treatment. IHCs or IFs can be co-registered on the image slide to obtain a quantification of the expressions of the biomarkers of interest. The quantification can be used for refinement of the predictive models of the system 200 and/or for better understanding of the disease or patient outcome.

Figure 3:
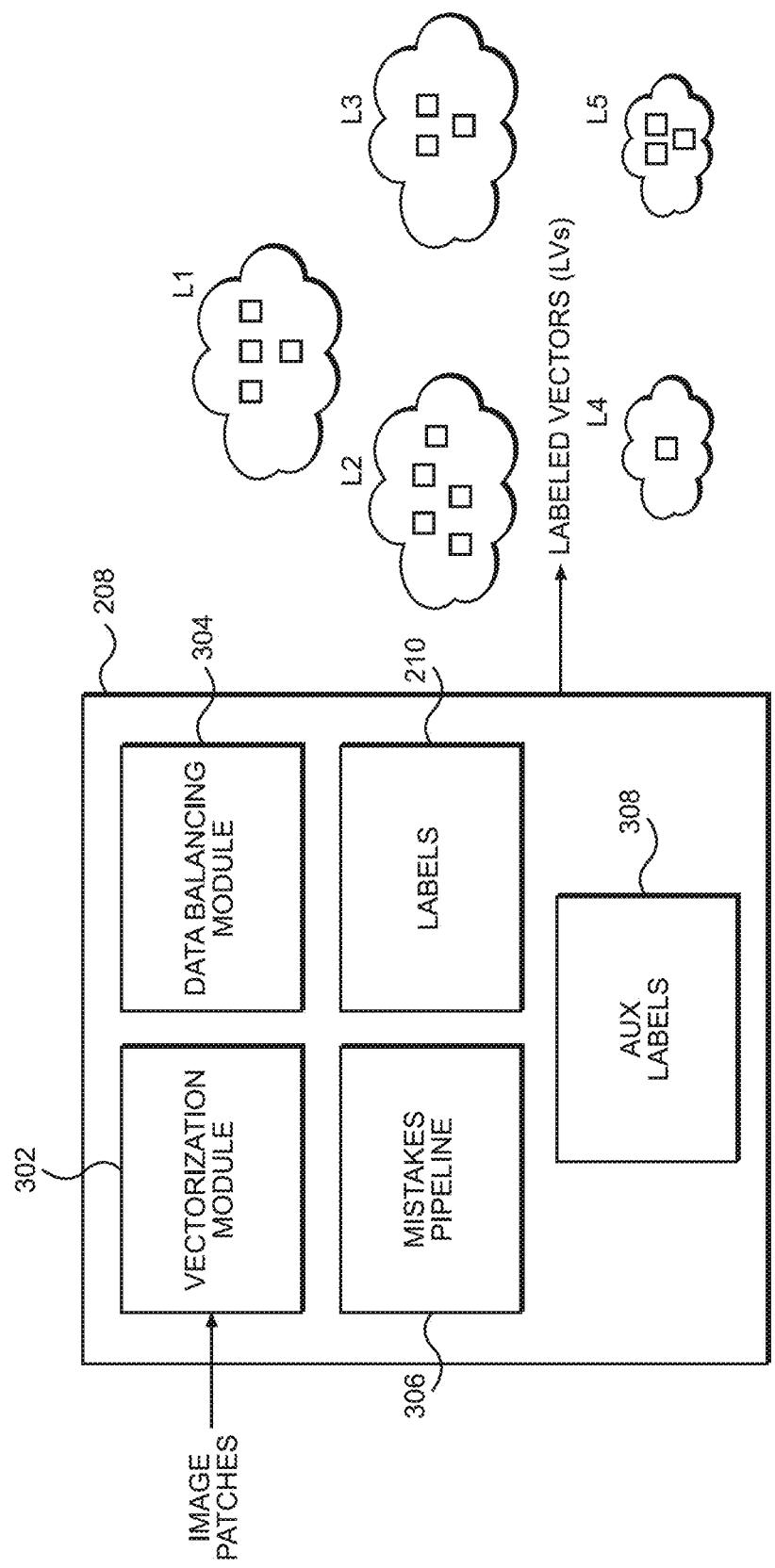
FIG. 3 illustrates a disease detection and grading module (DDGM) and the components therein according to an embodiment.

FIG. 3 illustrates the disease detection and grading module (DDGM) 208 and the components therein according to an embodiment. In one aspect, the DDGM 208 transform image patches into vectors. Image patches before vectorization are still a high dimensional data structure. For example, a patch of size 256 by 256 pixels, where each pixel has an RGB value is a data structure of 256×256×3 or a 196,608-value data structure. This high-dimensional data structure can be transformed to a vector of smaller size, using DDGM 208 and sub-morphology detector 212. For example, a patch can be vectorized based on whether the patch is identified to be from a benign tissue and within one of the detected sub-patterns of that benign tissue. In one aspect, the DDGM 208 and sub-morphology detector 212 convert a high-dimensional value patch to a more compact vector. Vectors that have similar mathematical representations can cluster together to identify a morphological sub-pattern.

Pathologists can annotate a set or subset of training images with labels 210. The Labels 210 can be a high-level annotation of morphological patterns that may occur in images 202 and 204. Example labels 210 can include, but not limited to, benign, cancer precursor, low, medium or high-grade cancers, immune cells, stromal cells, etc. The labels 210 can be based on morphological patterns known to pathologists used for cancer detection and grading. A vectorization module 302 can include one or more supervised artificial intelligence networks, including for example, neural networks, deep neural networks, convolutional neural networks (CNNs), and other artificial intelligence networks. The vectorization module 302 accepts as input image patches and using the labels 210 classifies the patches into the categories identified by labels 210. In the example shown, image patches are categorized between 5 labels L1-L5. As described earlier, in some embodiments, the labels 210 can include a high-level disease identification and a high-level grading of the detected disease. The DDGM 208 outputs a labeled vector for each input image patch, that places the patch in a category identified by labels 210.

The labels 210 may be high-level indications of morphological patterns. For example, there may be hundreds of morphological shapes and sub-patterns in which benign cells can appear on an image slide. Labels 210 may be at a high-level or high-abstraction level because labeling all the morphological sub-types that can appear in an image segment can be impractical, burdensome or difficult. Consequently, in regular clinical practice, a pathologist might label and rely on broad labeled categories. The DDGM 208 in combination with the sub-morphology detector 212 can further classify image patches based on the sub-types and sub-morphological categories to which they might belong.

Initially, the sub-patterns are broadly labeled using labels 210 (e.g., benign, cancerous, low, medium or high-grade cancer, immune, stroma) through the supervised learning processes of the DDGM 208. As will be described, the sub-morphology detector 212 uses an unsupervised learning method to extract sub-patterns that may be present in each label 210. In one embodiment, the labels 210 are based on the level of granularity that a pathologist might use to label images or image segments in her regular clinical practice. The artificial intelligence models of the vectorization module 302 can be trained to detect these labels in a set of input patches. In other words, the models of the vectorization module 302 learn morphological patterns and features corresponding to each label 210 and can distinguish and categorize the image patches based on those morphological features and patterns. In some embodiments, the last layer of prediction of the models of the vectorization module 302 can be used to extract a morphological vector corresponding to a patch, which can be used to represent the input data with less complexity, while retaining data relevant to patient outcome or response.

In one aspect, the input image data is heterogeneous and complex. When a pathologist examines an image segment (e.g., an image or image segment of a gland), they look at the nuclei, they look at the gland, and they look at the environment around the gland to make a judgment of whether it is cancerous or not. There may be some cells inside the gland that look cancerous, but the pathologist will still grade the whole gland as benign, if they see some other types of cells, which they know only show up in benign glands. The models of the system 200 and the DDGM 208 perform a similar function. The vectorization module 302 can include auxiliary labels 308 (e.g., nuclei, cytoplasm, gland, neighborhood, etc.). Image patches are also labeled according to auxiliary labels 308. In one embodiment, the models of the vectorization module 302 further classifies the image patches having auxiliary labels 308 at various sizes and resolutions. At the end of a last patch, the models of the vectorization module 302 can for example determine whether a patch has an auxiliary label 308 of a nucleus. The patch is processed through the vectorization module 302 at different resolutions, where it is determined if a label 210 is applicable to the patch, when the patch is viewed at different sizes and resolutions. For example, the vectorization module 302 can determine whether the nucleus is cancerous, benign, whether if the nucleus is in a gland, the gland is cancerous or not, and whether other cells within the neighborhood are cancerous or not. Based on the output of the processing of a patch at multiple resolutions and sizes, the vectorization module 302 can apply or modify a label 210 of the patch accordingly. This is similar to a process that a human pathologist might employ to apply a label 210 (e.g., cancer or not cancer) to an image patch. For example, in clinical practice, if a gland (viewed at high resolution) looks benign, but everything around it (viewed at lower resolution) is cancerous, a pathologist is more likely to conclude that that gland is also cancerous.

In other words, the models of the system 200, including the models of vectorization module 302 can operate on image data in the same way a pathologist might operate on the data (e.g., by labeling the image patches at various resolutions). Consequently, the models learn relevant and effective features, and learn to ignore artifacts. In some embodiments, image patches having been applied an auxiliary label 308 can be processed in the vectorization module 302 at a plurality of resolutions. As an example, an image patch can be viewed by the model and applied a label at three levels of resolution. Fewer or more levels of resolutions are also possible.

Furthermore, the input image data can be highly imbalanced in terms of the features that are relevant to patient outcome or patient response. In the case of cancer, a high-grade cancer may show up in less than 0.01 percent of the tissue. For example, 20-50 cells out of millions of cells on an image slide may be high-grade cancer cells. Those 20-50 high-grade cancer cells can change the treatment decision for the patient. A data balancing module 304 can balance the training data, so the models of the vectorization module 302 can give appropriate weight to morphological features that are highly relevant but may not occur in high frequency or quantity in the image slide. In some embodiments, the data balancing module 304 can use clustering to balance the input training data for the models of the vectorization module 302. The data balancing module 304 can cluster the input data based on morphology through an iterative process. The models of the vectorization module 302 are first trained using the baseline input image data, yielding a first level of accuracy. The output vectors are used to cluster the input image data and pass through the models of the vectorization module 302. Input training data, in subsequent passes, is fed uniformly through the models of the vectorization module 302 in a manner that input data from each cluster can be uniformly sampled throughout the input training data across all pattern subtypes, regardless of how frequently they show up in the tissue.

To further increase the accuracy of DDGM 208, a mistakes pipeline can use patch labels that are determined with less confidence and increase their presence in the input training data, so the models of the vectorization module 302 can better learn the low confidence labels. The vectorization module 302 may use a predetermined label threshold before classifying input data as belonging to a label. For example, one classification threshold of a label can be data having a score of 0.5 or more on a scale of 0 to 1. If data is classified with a score of 0.6. That data is classified with a confidence lower than another data, which is classified with a score of 0.9. Classifications with higher confidence score can increase the accuracy of the models of the vectorization module 302. The mistakes pipeline 306 can identify low confidence classification and sample them as input training data for the next round of training. In another embodiment, the mistakes pipeline can also sample from errors, as well as low-confidence classifications. In some embodiments, the mistakes pipeline is applied after the models of the vectorization module 302 have learned the labels that are easy to learn. In some embodiments, a predetermined percentage of the input training data to the AI models of the vectorization module 302 is used to feed input data from the mistakes pipeline (sampled from those input values that have generated output vectors having error or low confidence level).

Figure 4:
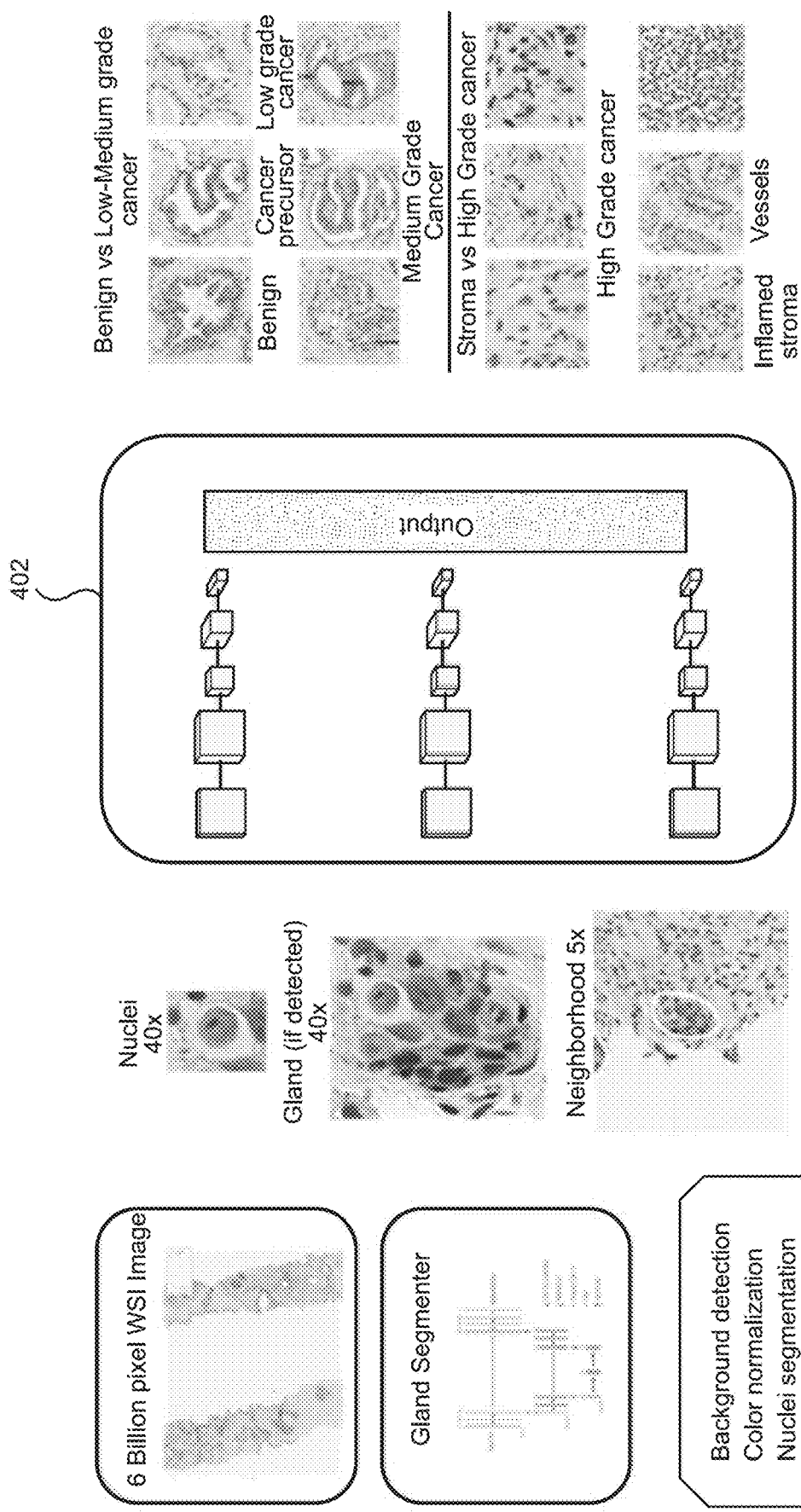
FIG. 4 illustrates an example implementation and operation of a vectorization module.

FIG. 4 illustrates an example implementation and operation of the vectorization module 302. Artificial intelligence models 402 can be trained to identify different morphological subtypes in H&E slides (or other input images if used). The ground truth for the model 402 can be provided by a group of experienced pathologists, who discuss, agree and then identify known morphology features such as benign glands, cancer precursors, low/medium/high-grade cancers, immune cells, stroma, etc. These labels are based on known morphological patterns that pathologists use for cancer detection and grading.

Additionally, as discussed earlier, the models 402 can be trained based on auxiliary labels 308 to provide more accurate identification and classification for the input data labeled with auxiliary labels 308 based on processing that input data at different sizes and resolutions. For example, for each nucleus that is labeled, three patches are generated (e.g., 64×64 pixels at 40×resolution, 256×256 pixels at 40×resolution and 1024×1024 pixels at 5×resolution). The inner most patch captures the nucleus; the middle patch captures the gland and the outermost patch captures the micro-environment of the nucleus. Three parallel CNNs are run to transform the patch to a 1024-dimensional vector. The 3×1024 vectors are combined and classified to one of the known labels. In other embodiments, fewer or more patches based on a detected nucleus can be generated. Other resolutions and sizes can also be used. In some embodiments, the patches are from a WSI image, which can include a large number of pixels (e.g., in the order of millions or billions). The DDGM 208 can include other modules to improve labeling the input data (by auxiliary labels 308 or by labels 210). For example, a background module, color normalization, gland segmenter or nuclei segmenter can be used to label input image patches.

As described earlier, training data can be highly imbalanced. For example, there can be a very small percentage of high-grade cancer (<0.01%) that can determine or change treatment. To balance the dataset, the vectors generated from the first pass of training can be used to divide the input training data into clusters of morphologically similar patterns. This clustering can be performed, so different sub-patterns of input data are equally represented in the input training data (in iterative passes), even though they may not be present in equal amounts in the training dataset, or in clinical practice.

The mistakes pipeline 306 can further fine-tune the models of the vectorization module 302. Patches that the model has detected with low confidence are identified, based on the absolute value of the difference between the confidence level and a predetermined threshold for a classification label. If the absolute value of the difference does not exceed a confidence threshold, the underlying input data or a sampled subset of the underlying data is fed through the mistakes pipeline 306 to the models 402, as part of the training data. Consequently, the models 402 can give appropriate weight to the low-confidence data. Additional patterns that show up in small quantities and cannot be captured through clustering, can also be fed into the mistakes pipeline 306 to further improve the accuracy of models 402.

In one aspect, the output of the DDGM 208 includes a detection of presence and grading of a disease (via classification in the labels 210) and vector representations for morphological types in that disease. These labeled vectors are fed into a sub-morphology detector (SMD) 212.

Figure 5:
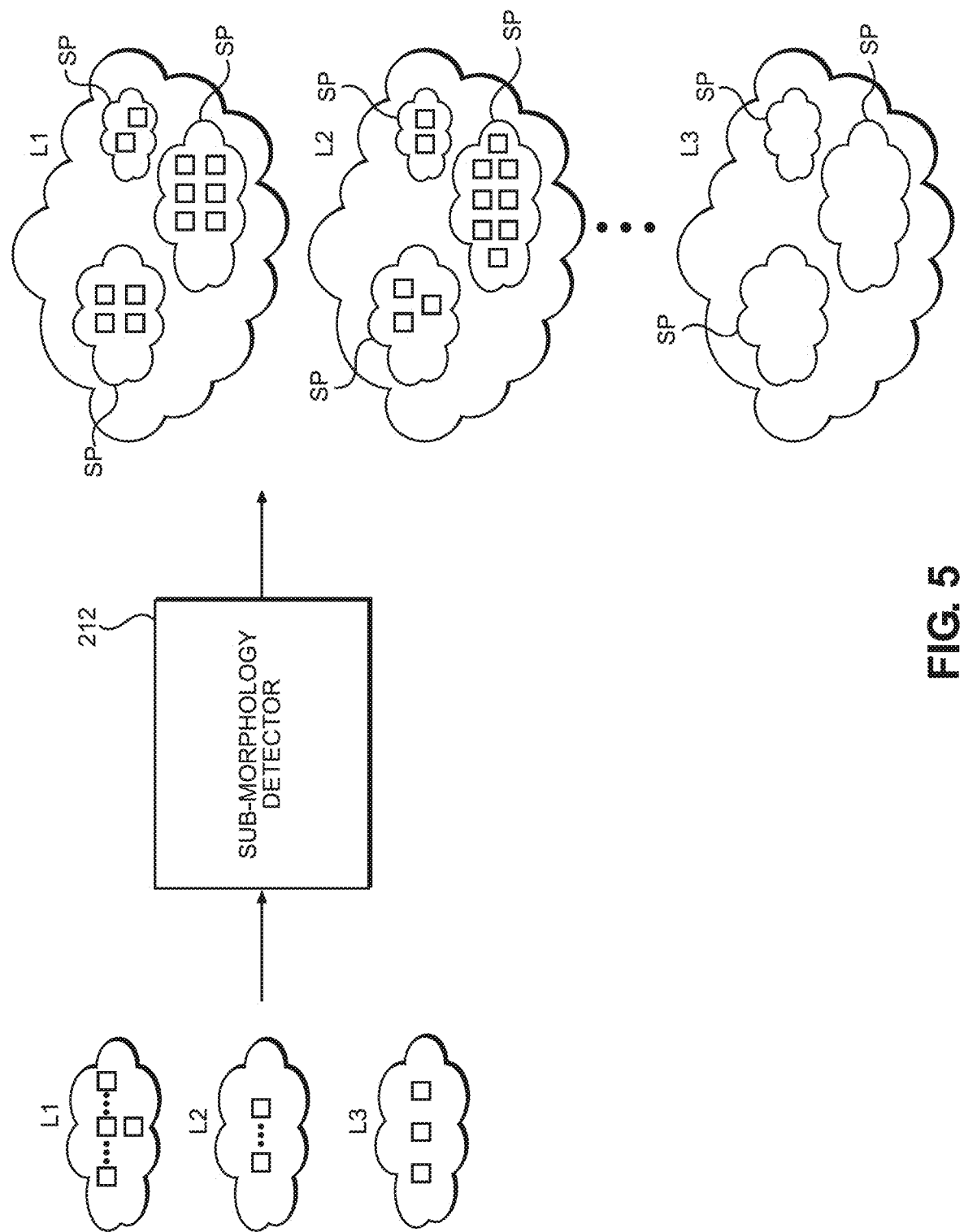
FIG. 5 illustrates a sub-morphology detector (SMD) according to an embodiment.

FIG. 5 illustrates a sub-morphology detector (SMD) 212 according to an embodiment. The operations of the SMD 212 will be described in relation to FIG. 5 and previous figures. The SMD 212 receives labeled vectors and detects further morphological sub-patters within each label category, using unsupervised learning algorithms, such as clustering analysis, principal component and other unsupervised machine learning techniques. To provide input to the SMD 212, patient input images 204 that are accompanied by patient outcome data are received. The input images 204 include patient clinical response or outcome data, such as patient response to a drug, response to a treatment option (including surgery, radiation, etc.), whether the patient experienced progression-free survival (PFS), number of months or years of PFS or any other outcome or response criteria that may be of interest to healthcare providers, and disease or treatment researchers.

Each patient slide is divided up to patches using the patch generator 206. As an example, each patient slide may be divided into 50 to 100K patches. Each patient patches and the patient outcome data are fed through the DDGM 208, which generates a labeled vector for each patch. Now, instead of a patch being an image, the patch is represented by a vector. The dimensions of the vector can be chosen according to an embodiment. Examples include 500, 1,000 or 2,000 dimensional vectors. These vectors can inherently capture similarities, which correspond to morphological similarity on a tissue slide. In other words, patterns that are morphologically similar, have mathematically similar vectors. In one embodiment, for example, the cosine function can be used to cluster similar vectors. Vectors that are mathematically similar yield cosine function results that are close in range. Other vector operations can also be used to determine similarity between vectors. In one respect, the SMD 212 converts an image into a structured dataset that can be used to rank and score image patches in terms of patient response or outcome.

Figure 6:
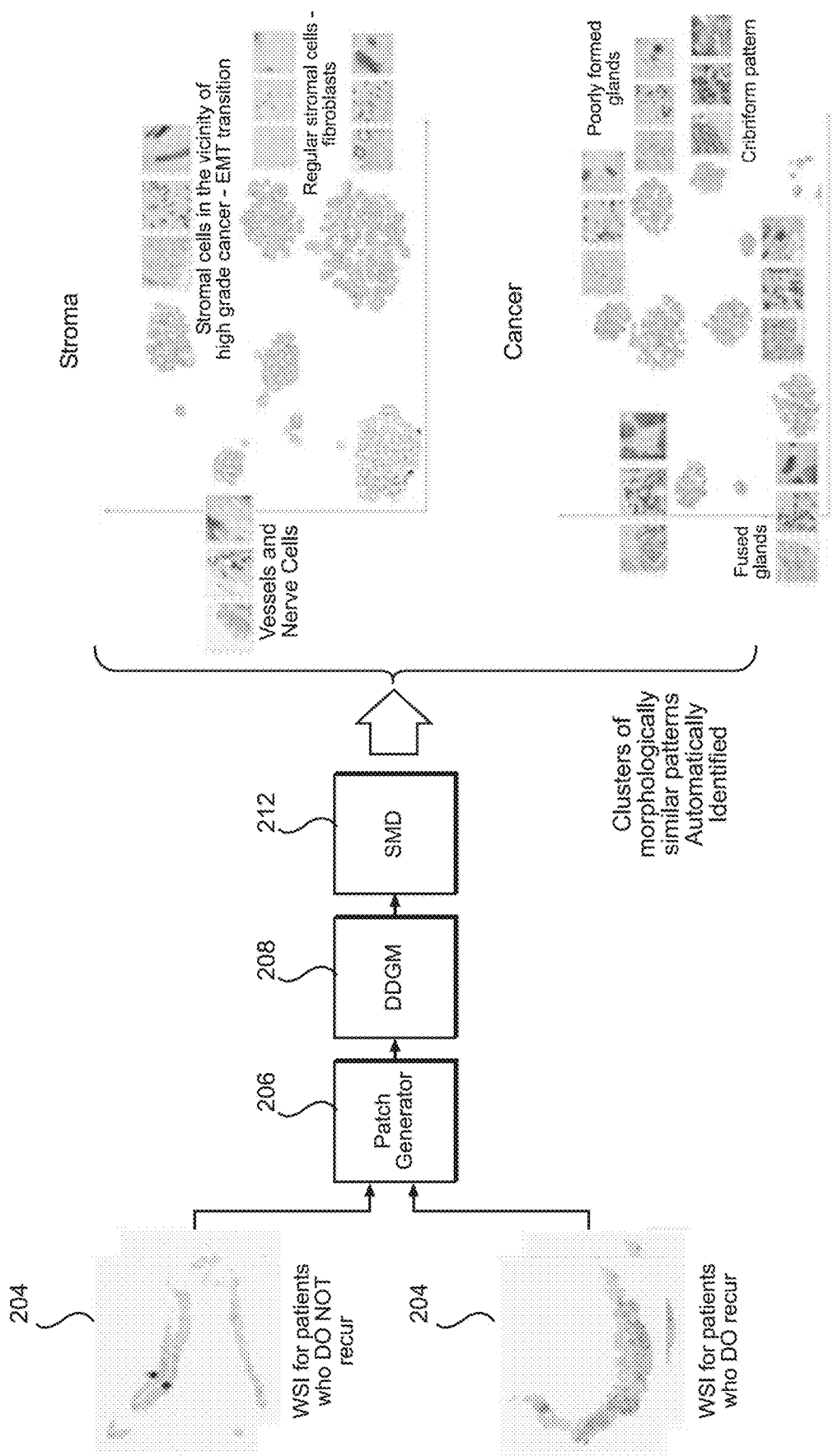
FIG. 6 illustrates an example operation of the SMD according to an embodiment.

FIG. 6 illustrates an example operation of the SMD 212 according to an embodiment. In one aspect, the SMD 212 can extract morphological sub-patterns within a label (applied by DDGM 208) by using unsupervised learning techniques. Input images 204 can include WSI from patients with known clinical outcomes, including those whose disease has recurred and those who have not experienced recurrence. Other potential patient outcomes can include initial response, progression free survival (PFS), overall survival (OS) or other criteria of interest to the clinicians and the researchers. Therefore, the input data can include both patients with positive, as well as adverse outcome. For each patient, the H&E WSIs 204 (or other input images 204 if used) are divided into patches by the patch generator 206. In one embodiment, the size of the patches can be 256×256 pixels at 40× resolution. The patch generator can be configured to generate patches of different sizes depending on the implementation and as input to other modules (e.g., to DDGM when patches of different sizes and resolutions are used to label the input data based on auxiliary labels).

Next, the DDGM 208 can predict a label 210 for each patch. In one embodiment, where three parallel CNNs are used to implement the DDGM 208, the last layer of the vectors is extracted, and used as the vector representation of the patch. As an example, in the three-parallel net architecture, if each vector is of size 1024, the last vector chosen for vector representation of the patch is of size 3×1024 or 3072.

Next, the SMD 212 clusters the vectors to identify morphological sub-patterns within each label. This can generate hundreds of clusters of morphologically similar patterns that do may not have an explicit label but can represent a phenotype. In the example shown, multiple morphological sub-patterns are identified for stroma and cancer labels. The morphological sub-patterns identified by SMD 212 can include regions that in turn include biomarkers, signals or signatures of disease or patient outcome that may have been previously unknown in ordinary clinical practice.

The DDGM 208 and SMD 212 convert unstructured data of gigapixel WSIs (or other input images if used) to a structure of clusters of morphological patterns. This structured representation of morphology enables downstream tasks of ranking these patterns and identifying which patterns are prognostic/predictive of patient outcome.

Figure 7:
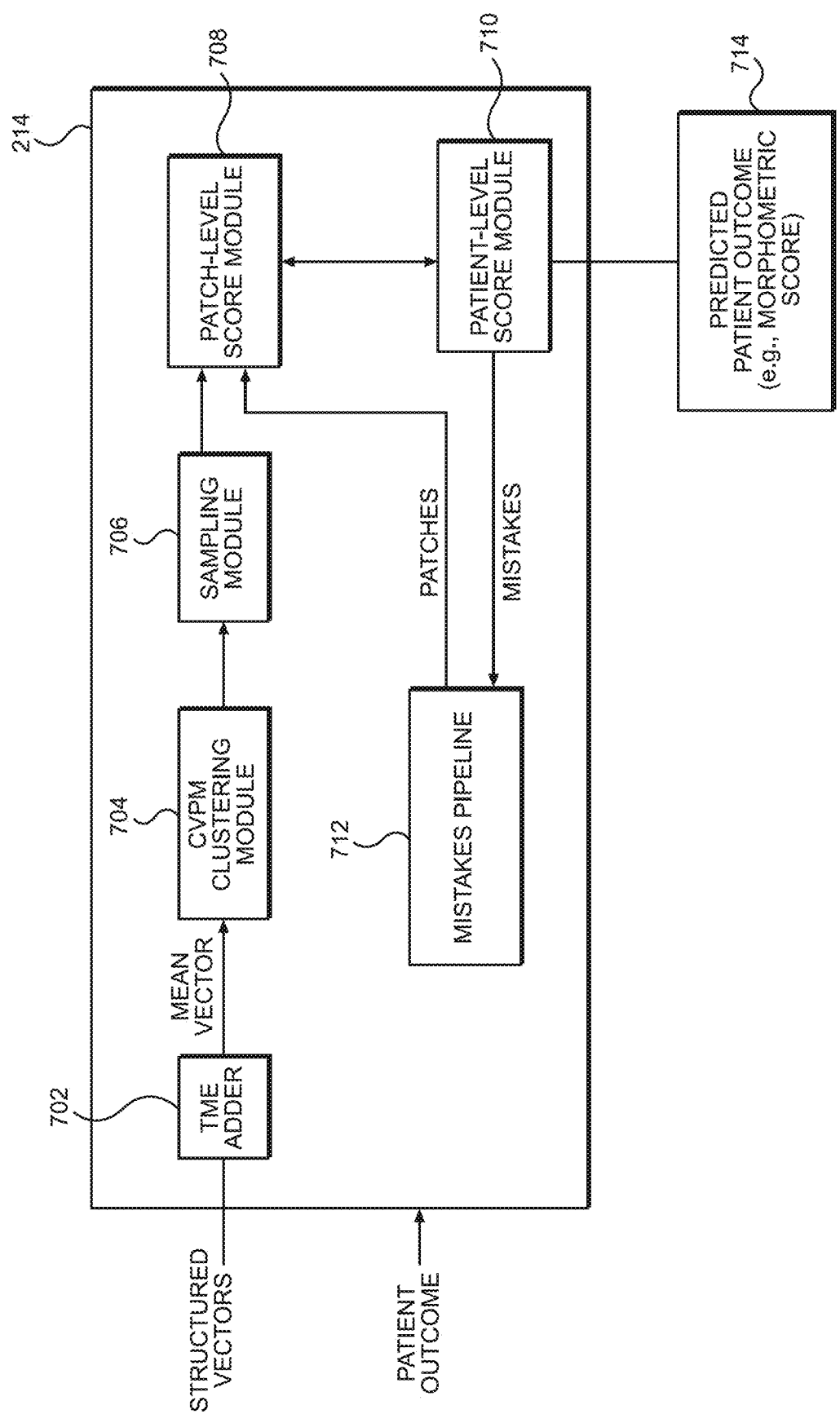
FIG. 7 illustrates a ROI and outcome prediction module (ROPM) and the components therein according to an embodiment.

FIG. 7 illustrates the ROI and outcome prediction module (ROPM) 214 and the components therein according to an embodiment. The ROPM 214 receives as input, structured vectors (or structured vectorized image patches) from the conversion of patient image data to structured vectors that identify labels 210 and morphological sub-patterns within each label 210. At patch-level score module 708, an artificial intelligence model can be trained to learn how to rank each patch to arrive at a patch-level score. A patient-level score module 710 can combine patch-level scores to arrive at a patient-level score indicative of a prediction of that patient's response to treatment. In one aspect, the weights of the artificial intelligence model of the patch-level score module 710 are used to arrive at a ranking or score for patches. The ROPM 214 can also receive, as part of training data, patient outcome along with the patient input images, patches and corresponding vectors. The AI model of the patch-level score module 708 fine-tunes its weights when it mis-predicts. In some embodiments, the model minimizes an error function using known patient outcomes as training data. In one respect, The ROPM 214 receive as input structured vectors, which can still be 1000-dimensional vectors and converts them into patch-level scores. In some embodiments, the patch-level score is a number between 0 to 1. The closer the score to 1, the higher likelihood that the underlying morphological sub-pattern contains a signal for adverse outcome. The closer the score to 0, the higher likelihood that the underlying morphological sub-pattern contains a signal for good patient outcome or response to treatment.

The input to the patch-level score module 708 can include a patch and the microenvironment of the patch. In some cases, the patch alone may not capture enough information to accurately score the patch. A TME adder 702 can be configured to obtain a region of predetermined size around a patch (e.g., by using patch generator 206) and vectorize the region (e.g., by using DDGM 208 and/or SMD 212). The region surrounding a patch can be chosen to capture the microenvironment of a patch. The data of the patch and its surrounds (e.g., microenvironment of the patch) can be used as input data to the patch-level score module 708 to generate a score for the patch. As an example, in some embodiments, the microenvironment of a patch can be chosen as a region of 3×3 or 5×5 pixels surrounding a patch. The TME ADDER 702 can combine the vectors from the microenvironment region with the vectors from the patch region. In some embodiments, the combination vector can be a mean vector. Other mathematical techniques combining the microenvironment vectors and the patch vectors are also possible candidates. Combining microenvironment vectors and patch vectors can allow for scoring a patch not only based on any tumor that may be present in the patch, but also the microenvironment of the tumor. The morphological manifestation of a tumor can look different in different regions of tissue based on the cells surrounding the tumor, and the microenvironment of the tumor in general. Consequently, the complexity of the microenvironment of the tumor cells can be captured via combining vectors from the microenvironment region with the patch vectors where the tumor may be present. The combined vectors of patch and microenvironment (CVPM) can be clustered into multiple clusters using a CVPM clustering module 704. As an example, 50 to 100K patches for a patient slide can be converted to 100 to 200 distinct clusters of CVPM. This can substantially reduce the complexity of the input image data and provide further structure for processing of the patient data and arriving at a prediction score.

Clusters of CVPM can include different numbers of corresponding patches because the morphological patterns in each cluster can occur with different frequencies in a WSI image or other patient input image. Nonetheless, frequency of occurrence of a morphological pattern may or may not have relevance to patient outcome. Some infrequently occurring morphological patterns can nevertheless be clinically significant for patient outcome and response. A sampling module 706 can sample input training data from each cluster in a manner that exposes the AI model of the patch level score module 708 to data in a uniform matter, regardless of the volume and frequency of patches in the clusters. In other words, sampling module 706 can be used to input a uniform representation across the morphological subtypes in a patient slide.

The path-level score module 708 can include a deep learning artificial intelligence model that uses its weights to assign a score to each patch. In other words, the AI model of the patch-level score module converts a CVPM to a score (e.g., a number between 0 to 1). A patient-level score module 710 takes a predetermined sampling of the patch-level scores and combines them to arrive at a patient-level score. In one embodiment, a predetermined number of top patch-level scores and a predetermined number of low patch-level scores are combined to arrive at a patient-level score. During training, the patient-level score is compared against known clinical patient output. If the results do not match, the weights of the model associated with the sampled patch-level scores are modified to find a better weight distribution that yields a patient-level score closer to the known clinical patient outcome. In one respect, the combination of all patch-level scores are not used, so the model can remember weights associated with which patch-level scores need to be modified in order to fine-tune the predicted patient-level score. In another respect, the ROPM 214 and the AI model therein learn to predict patient outcome, and in the process, learn to rank patches in a manner that yields an accurate patient outcome prediction. Consequently, patch-level scores can yield regions of interest that likely contain predictive biomarkers, signatures and signals.

In some embodiments, the ROPM 214 includes a mistakes pipeline 712, which is similar in operations to the mistakes pipeline 306 as described above. The mistakes pipeline 712 identifies patches, which the model has not learned well and allocates a percentage of the input data in subsequent passes to those patches, so the model is exposed to and can learn those patches better. The mistakes pipeline 712 can determine which patches correspond to a mistaken prediction, where a mistaken prediction can refer to the output 714 of patch-level score module 708 and patient-level score module 710, at the end of a training pass, predicting an outcome for the patient that does not match the known clinical outcome of that patient. For example, if a patient is non-recurrent, but the output 714 of ROPM 214 is predicting the patient has recurrence. In this mistaken prediction scenario, there are patches that show up on the patient's image slide that the model of the ROPM 214 is allocating high values, where the high values given to those patches can cause the combined patient-level score for that patient image slide to be above a predetermined threshold, and the model is predicting that the patient is recurrent. Conversely, the model of the ROPM 214 may be allocating lower value weights to some patches that should otherwise be scored higher, causing a mistaken prediction of non-recurrent, where the known clinical outcome of the patient is recurrent. The mistakes pipeline 712 can identify patches that are causing mistaken predictions, and feeds those or a sampled subset of them as training input data in successive training passes to the models of ROPM 214. Consequently, the models of the ROPM 214 get exposed more in iterative and successive passes to the patches that the models do not accurately score and learn to score those patches more accurately. In one respect, the mistakes pipeline 712 performs a tuning step, similar to mistakes pipeline 306, where the AI models are first train based on cluster of patches until an initial level of accuracy is reached. After the model is mature and it is still making some mistakes, the training data of the model will be sampled in a way to include a predetermined percentage of mistakes from the mistakes pipeline 712 to train the model for better accuracy regarding those elements that are causing a mistaken output.

The output 714 of ROPM 214 can include patient outcome or response indicator in the form of a morphometric score. In some embodiments, the morphometric score is a number between 0 to 1 that indicates a risk profile of a given patient. The closer the morphometric score of a patient to 1, the higher risk of an adverse outcome for that patient. The output of the patch-level score module 708 also includes scores that indicate risk of correlation between that patch and the patient outcome. Therefore, the patch-level scores can be used to identify regions of interests (ROIs) for further analysis and for finding biomarkers, signatures or signals predictive of patient outcome.

Figure 8:
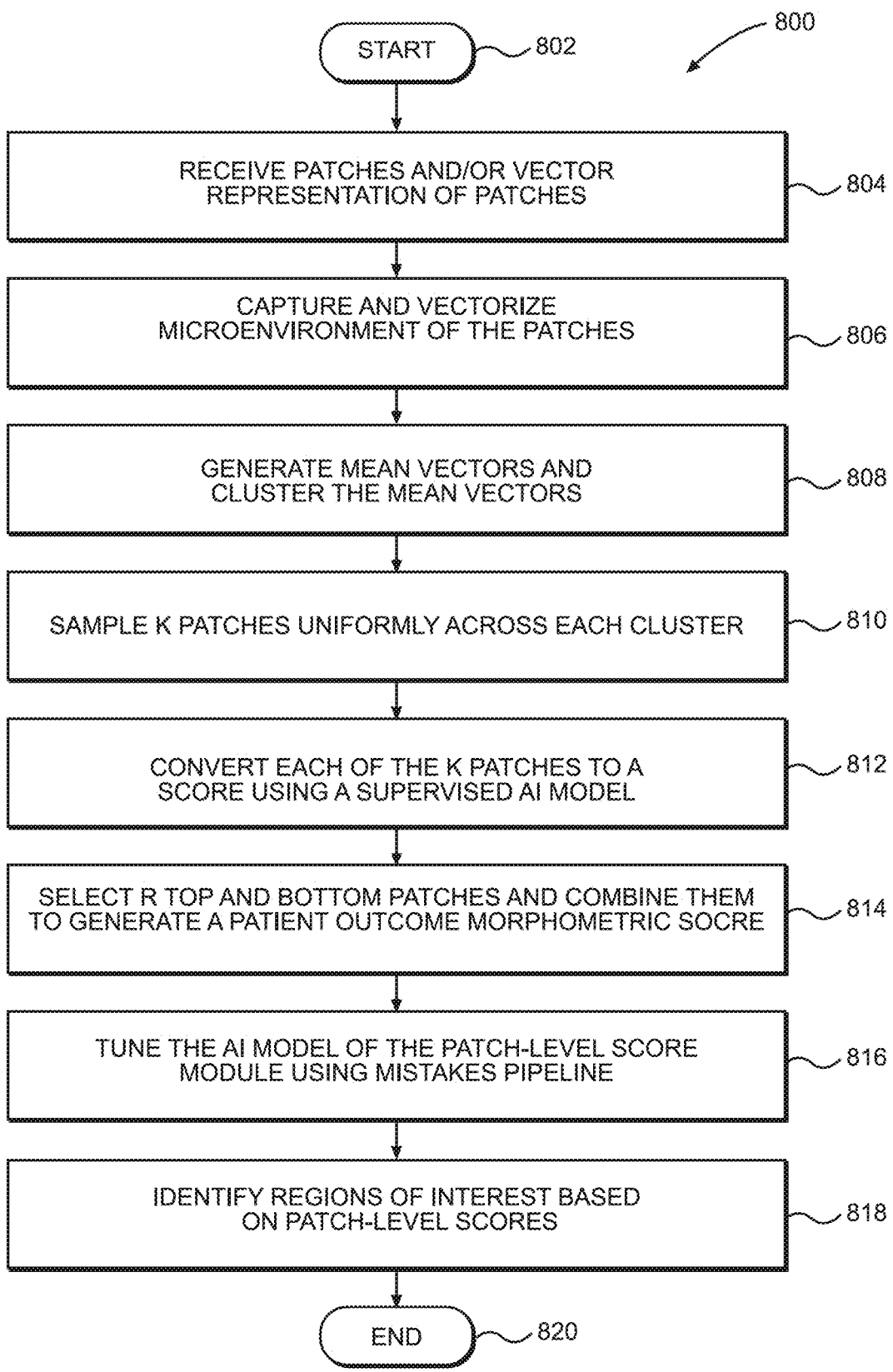
FIG. 8 illustrates a flowchart of a method of the operations of the ROI and outcome prediction module (ROPM) according to an embodiment.

FIG. 8 illustrates a flowchart of a method 800 of the operations of the ROI and outcome prediction module (ROPM) 214 according to an embodiment. The module takes as input patch-level vector representations and generates a rank for each patch based on patient outcome. It can also generate a predictor of patient response or outcome as a morphometric patient outcome score. The method starts at the step 802.

At step 804, for each patient, the patches and corresponding vector representations for the patient image slides are collected. At step 806, to capture the micro-environment of each patch, an N×N region is selected around each patch, and the vectors of those regions are generated. At step 808, the vectors are averaged to generate a mean vector for each region. The mean vectors are clustered per label to generate multiple clusters. As an example, this can convert 50-100k patches into 100-200 distinct morphological clusters. At step 810, K numbers of patched are sampled uniformly across each cluster to generate a batch of vectors that represent the patient slides.

At step 812, each of the K patches are converted to a patch-level score between 0 and 1, using a supervised deep learning model, which is trained based on patient outcome. A high score (around 1) represents that the patch shows up in patients with adverse outcome, while a low score (around 0) represents good outcome (e.g., the patch appears in patients with non-recurring cancer). The patch-level scores are generated using a set of weights in the deep learning model that are learned by the outcome based on known patient outcome as labels.

At step 814, the top and bottom R patches are selected and combined to generate an outcome morphometric score for the patient. As described above, choosing a limited predetermined set of patches to be responsible for the outcome morphometric score can force the deep learning model to learn the most predictive features and give them the highest or lowest scores. At step 816, the deep learning model is further fine-tuned using a mistakes pipeline. Patches are identified that are causing mistakes in predicting patient outcome. These patches are collected and used to generate training data to expose the deep learning model to learn the mistakes better and assign more accurate weights to them. At step 818, based on patch-level scores, regions of interest (ROIs) are identified on the tissue slide. The method ends at step 820.

Figure 9:
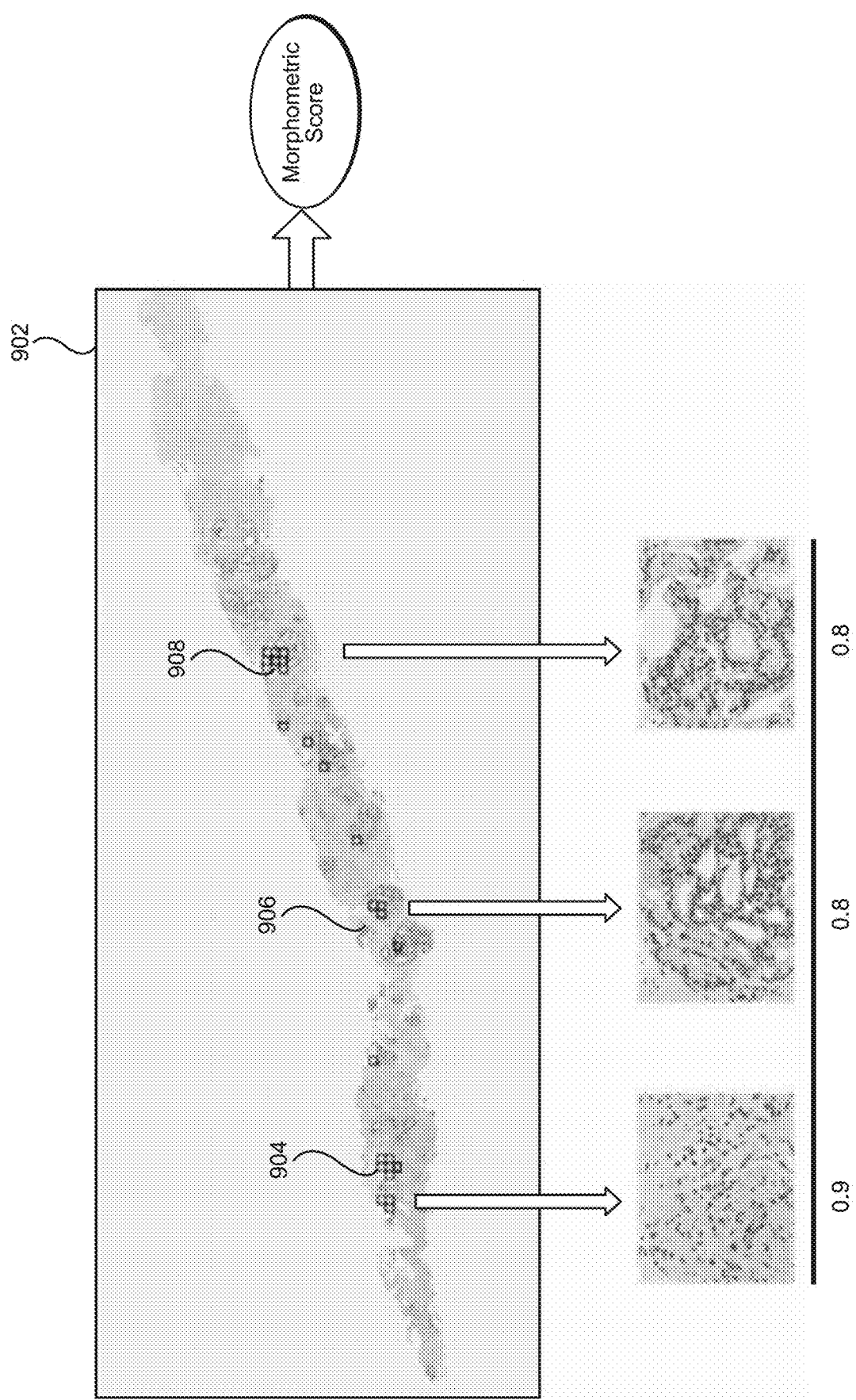
FIG. 9 illustrates a tissue slide that has been processed through the patient outcome prediction system.

FIG. 9 illustrates a tissue slide 902 that has been processed through the patient outcome prediction system 200. Various clusters of morphologically similar features have been identified. The regions 904, 906 and 908 have been assigned a high patch-level score, indicating those regions are likely strongly correlated with adverse patient outcome (in the form of a morphometric score showing high adverse outcome risk). The regions 904, 906 and 908 are therefore regions of interest (ROIs) that can be further analyzed for determining potential drug or treatment targets and/or biomarkers indicating patient outcome or response. Without identification of ROIs, such as regions 904, 906 or 908, a pathologist would have to analyze the entire tissue slide 902 to determine information related to patient outcome or treatment response. This analysis can typically involve techniques, such as DNA/RNA and protein analysis that would be too burdensome or impractical to perform for a patient. Instead, given the ROIs 904, 906 and 908, a pathologist's effort can be focused and targeted to a much smaller number of cells.

Having identified ROIs, molecular analysis or other techniques can be applied to those regions to determine which gene mutations or cellular processes are causing the patient to exhibit the morphological regions that are indicative of adverse outcome. This platform allows classifying tissue globally based on the protein and mRNA expression in ROI obtained through unsupervised morphological features extraction or focus on any region of interest to discover novel gene expression profiles. Combining gene expression profiles/signature found through protein and RNA analysis with morphological context of ROI (clusters of regions 904, 906 and 908) and non-ROI (other regions or patches which shows low score) in a wide variety of tissue types and their correlation with patient survival or therapy response outcome helps to discover precise biomarker signature for predicting outcome. For example, spatial profiling and biomarker identification techniques can be applied to the ROIs.

Figure 10:
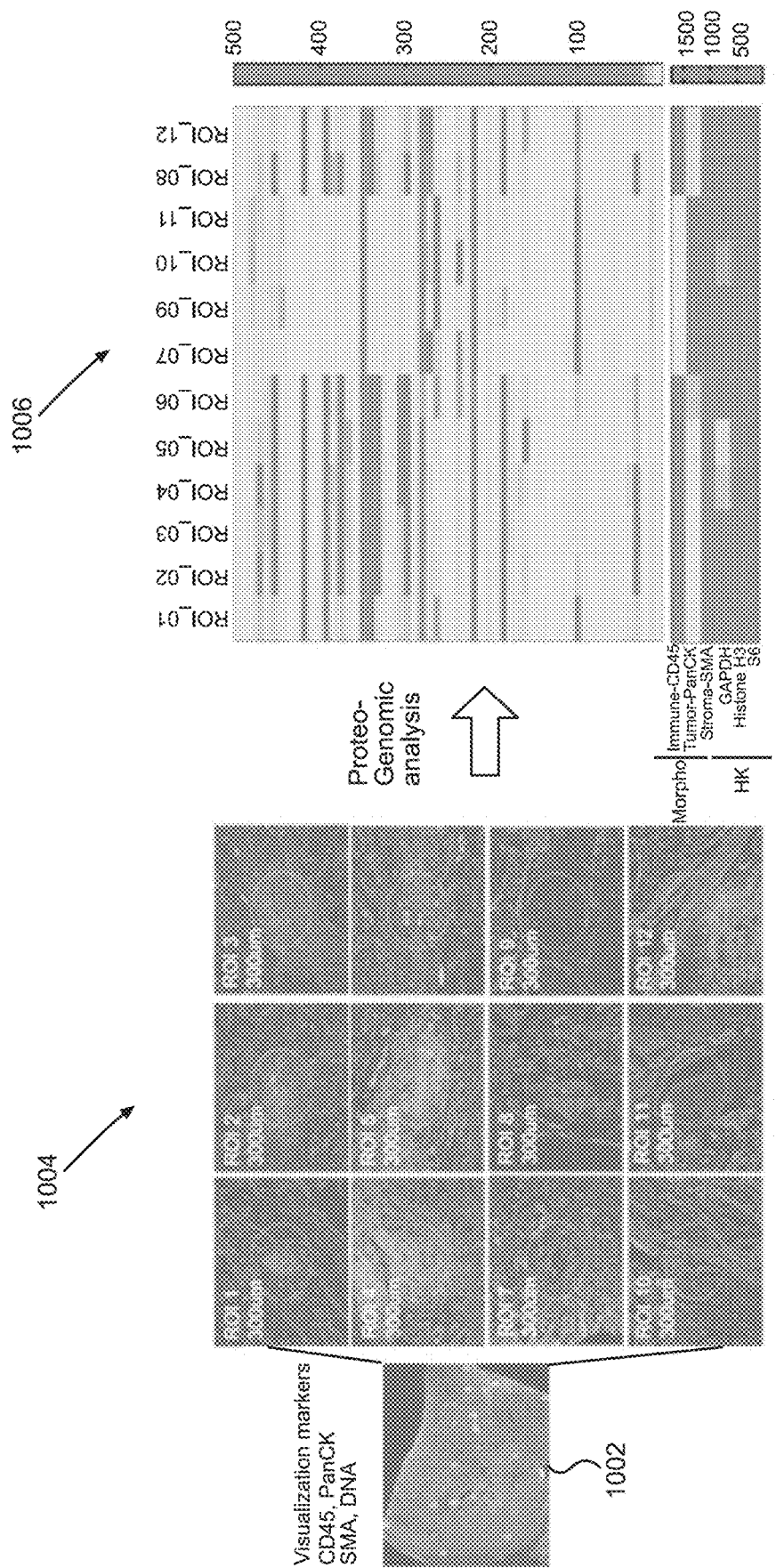
FIG. 10 illustrates an application of proteo-genomic technique to regions of interest identified by ROPM to determine proteins or DNA/RNA markers that correlate with patient outcome.

FIG. 10 illustrates an application of proteogenomic technique to regions of interest identified by ROPM 214 to determine proteins or DNA/RNA markers that correlate with patient outcome. The ROIs can be stained with multiple epithelial, immune and stromal markers to identify protein/RNAs that are over- or under-expressed in the ROIs compared to non-ROIs. These markers capture molecular pathways that are driving or at least correlate with the morphological changes in the ROIs and can be predictive of patient response or outcome. Included in the analysis are different types of nonmalignant cells that may be constituents of the tumor microenvironment such as immune and stromal cells. These cells are known to differentiate into subtypes with distinct roles, and this process involves in reprogramming to satisfy their cell autonomous demands and enable interactions with other cell type. Different ROI has same or different proteins/RNAs signature-based pathway enrichment specifically expressed in these specific cell types. In one embodiment, gene set enrichment analysis (GSEA) is performed to compare gene expression between two different subtypes or ROI correlated to patient outcome and to identify different pathways enriched in each subtype/ROI. Significant enrichment of several pathways that distinguished two different cell types or ROI is found, and enrichment of one particular pathway in one or more ROI compared to non-ROI or correlated to patient outcome is found.

In the example of FIG. 10, the tissue slide 1002 is processed through the described embodiments and 12 regions of interest (ROIs) 1004 are identified. Proteo-genomic analysis on the ROIs vs. non-ROIs regions of the slide 1002 is performed as shown in the graph 1006, yielding differential expressions of protein/RNA between ROIs and non-ROIs. The ROIs can be obtained from patches having high patch-level scores near 1 and non-ROI regions can be obtained from patches having low patch-level scores near 0. The differential expressions of protein/RNA can identify biomarkers (e.g., proteins) that are over- or under-expressed in the ROIs vs. non-ROI regions.

Proteogenomic analysis or other biomarker identification techniques allow for detection of markers, including but not limited to immune markers, cancer markers, stromal markers, etc. that may be over- or under-expressed in ROIs compared to the non-ROIs. Without the benefit of ROIs determined by the ROPM 214, molecular markers are searched for at the whole slide level, while the information, related to differential (up-regulation/down-regulation) expression of genes related to specific pathways in ROIs vs non-ROIs and proteins to remodel the tumor microenvironment, is lost or weakened at the whole-slide-level analysis. This suggests that subpopulations of immune cells in the tumor microenvironment have specific features that differ from their behaviors in normal tissues and identify phenotypes that potentially help establish their roles in interacting with other cell types and modulating the tumor microenvironment. On the other hand, the problem with searching the whole slide for biomarkers, as is currently used in some existing techniques, is that any present disease signature is averaged out over the whole tissue, weakening the disease signal by including elements that are not biomarkers, weakening or hindering detection of biomarkers.

When biomarkers (e.g., proteins) predictive of patient response or outcome are identified, it can be beneficial to determine the spatial distribution of those biomarkers across tissue slides. Spatial distribution data can help improve the signature, because there may be elements that are not visible on an H&E slide but may be visible on a biomarker-specific IHC or IF stained image slide that captures spatial distribution of a biomarker. In other words, there may be more relevant or subtle patient outcome or response data that are only visible on biomarker slides. Without the benefit of having identified biomarkers predictive of patient response, it would be burdensome or impractical to develop biomarker slides for all potential biomarkers (e.g., in some cases 20,000 proteins can be potential biomarker candidates. Developing biomarker slides for these many proteins would be burdensome or impractical. Once the set of potential biomarkers is narrowed down, the spatial distribution of those signals can be developed by overlying or co-registering an annotated H&E slide with a biomarker slide, such as IHC or IF, where the annotations include patch-level morphological patterns. From the overlay, tumor cells and the proteins expressed by them are identifiable. The predicted patient outcome or response can be explained biologically as well.

Figure 11:
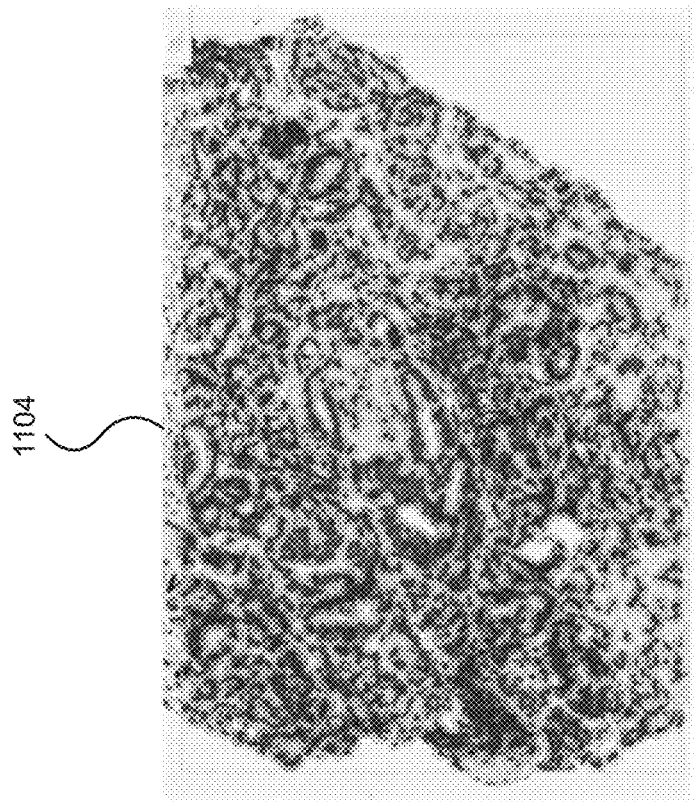
FIG. 11 illustrates an H&E image slide annotated with patch-level morphological patterns, using the described embodiments.
Figure 11:
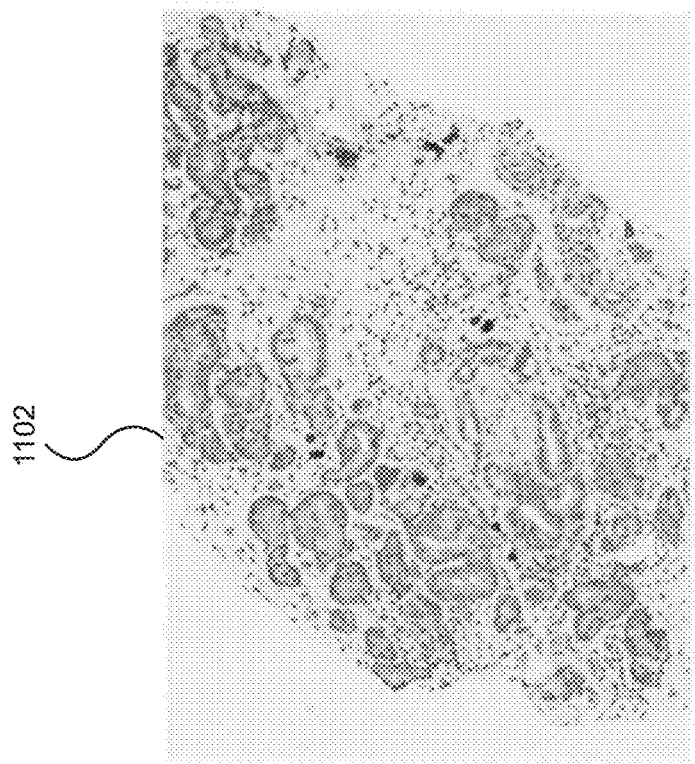

FIG. 11 illustrates an H&E image slide 1102 annotated or co-registered with patch-level morphological patterns, using the described embodiments. Biomarker slides can be developed for the annotated patch-level morphological patterns and for regions that have obtained a high patch-level score, as an example, indicating biomarkers predictive of patient response and/or outcome. The biomarker slides can be developed using a variety of techniques. As an example, the biomarker slide 1104 is generated using IHC imaging of two parallel FFP sections. The biomarker slide 1104 is superimposed with the annotated morphological patterns (or slide 1102) to allow for identification of spatial distribution of the biomarker for which slide 1104 was generated. Generating biomarker slides, such as the biomarker slide 1104 at a whole-tissue level and for every protein candidate can be burdensome or impractical, but given the benefit of the patch-level scores of the described embodiments and the identification of a more limited set of candidate biomarkers, the biomarker slides can be generated and used to gain further insight into the chemical or biological pathways of a disease, treatment or patient response/outcome to disease or treatment. In some embodiments, such insight gained from co-registering the morphologically annotated slide with the biomarker slides can be used to improve the accuracy of the AI models used in the patient outcome prediction system 200.

What is claimed is:

1. A method of predicting patient response to therapy, comprising:
   receiving a plurality of patient tissue image slides;
   receiving a plurality of patient outcome data;
   dividing the image slides into patches;
   receiving a plurality of labels correlated with a disease or lack thereof, wherein each label comprises of a morphological type, wherein a morphological type corresponds to molecular changes associated with the disease or lack of molecular changes associated with lack of the disease;
   converting each patch to a patch vector;
   training an artificial intelligence network, based on the plurality of labels to identify the morphological types associated with each label in the image slides;
   generating labeled patch vectors, wherein the label of a patch vector is assigned based, at least partly, on the plurality of the labels and the morphological type expressed in the patch;
   clustering the labeled patch vectors, within each label, with an unsupervised artificial intelligence network, wherein the clustering groups the patch vectors within each label to one or more morphological subtypes expressed in the patch corresponding to the labeled patch vector and a patient outcome, wherein clustering comprises clustering similar patch vectors within each label, and wherein morphological subtypes comprise unknown morphological sub-patterns within a morphological type;
   generating a patch-level score for each patch based at least partly on the cluster to which the patch vector of the patch belongs;
   generating a patient-level score for each patient, at least partly based on the patch-level scores generated for each patient; and
   predicting a patient response to a therapy, based at least in part, on the patient-level score for the patient.

2. The method of claim 1, wherein generating the patch-level score further comprises:
   converting regions surrounding each patch to microenvironment vectors;
   obtaining mean vectors by averaging the patch vectors corresponding to the patches with the microenvironment vectors;
   clustering the mean vectors;
   sampling input mean vectors from each cluster; and
   using an artificial intelligence model, comprising a plurality of weights, convert each sampled input mean vectors to a patch-level score.

3. The method of claim 2 further comprising:
   selecting a first group of patches having highest patch-level scores amongst the patch-level scores;
   selecting a second group of patches having lowest patch-level scores amongst the path-level scores;
   combining the first and second groups; and
   generating the patient-level score.

4. The method of claim 3 further comprising:
   comparing the patient-level score for a patient to the patient outcome data; and
   if the patient-level score does not align with the patient outcome data modify the weights of the artificial intelligence model.

5. The method of claim 1 further comprising identifying regions of interest in the patient image slide, at least partly based on the patch-level scores, wherein the regions of interest comprise biomarkers predictive of patient outcome.

6. The method of claim 5 further comprising:
   performing molecular analysis on the regions of interest; and
   identifying biomarkers based at least partly on differential expressions of biological macromolecules, comprising DNA, RNA or proteins, on the regions of interest versus other regions of the patient tissue image slide, wherein the biomarkers are over or under expressed in the regions of interest versus other regions.

7. The method of claim 5 further comprising:
   generating a biomarker slide based on the identified biomarkers;
   generating a patient image slide annotated with the regions of interest; and
   co-registering the biomarker slide and the annotated patient tissue image slide.

8. The method of claim 1, wherein generating labeled patch vectors further comprises:
   receiving a plurality of auxiliary labels; and
   when an auxiliary label is applicable to a patch vector or its corresponding patch, determine the label of the patch by processing the patch through the artificial intelligence network at a plurality of distinct sizes and/or resolutions.

9. The method of claim 1, further comprising:
   clustering the input training data of the artificial intelligence network based, at least partly, on the output vectors of the artificial intelligence network, wherein the output vectors of the artificial intelligence network indicate an underlying morphological pattern in the patient image slide; and
   sampling uniformly across the clusters of the input training data in subsequent training passes of the artificial intelligence network.

10. The method of claim 1, further comprising:
    assigning labels to patch vectors based, at least partly, on a confidence level;
    determining label assignments having a low confidence level;
    determining input patch vectors generating the low confidence level assignments; and
    sampling input training data of the artificial intelligence network to include a pre-determined percentage of input training data from the input patch vectors having generated low confidence level assignments in previous training passes of the artificial intelligence network.

11. A system of predicting patient response to therapy, comprising:
- a patch generator configured to receive a plurality of patient tissue image slides and divide the image slides into patches;
- a disease detection and grading module, comprising an artificial intelligence network, wherein the disease detection and grading module is configured to:
  - receive patient outcome data;
  - receive a plurality of labels correlated with a disease or lack thereof, wherein each label comprises a morphological type, wherein a morphological type corresponds to molecular changes associated with the disease or lack of molecular changes associated with lack of the disease;
  - covert each patch to a patch vector;
  - train the artificial intelligence network, based on the plurality of labels to identify the morphological types associated with each label in the image slides;
  - generate labeled patch vectors, wherein the label of a patch vector is assigned based, at least partly, on the plurality of the labels and the morphological type expressed in the patch;
- a morphology detector comprising an unsupervised machine learning model configured to cluster the labeled patch vectors, within each label, wherein clustering groups the path vectors within each label to one or more morphological subtypes expressed in the patch corresponding to the labeled patch vector and a patient outcome, wherein clustering comprises clustering similar patch vectors within each label, and wherein morphological subtypes comprise unknown morphological sub-patterns within a morphological type; and
- a region of interest and outcome prediction module configured to:
  - receive the clustered labeled vectors and generate a patch-level score for each patch based at least partly on the cluster to which the patch vector of the patch belongs;
  - generate a patient-level score for each patient, at least partly based on the patch-level scores generated for each patient; and
  - predict a patient response to a therapy, based at least in part, on the patient-level score for the patient.

12. The system of claim 11, wherein generating the patch-level score further comprises:
- converting regions surrounding each patch to microenvironment vectors;
- obtaining mean vectors by averaging the patch vectors corresponding to the patches with the microenvironment vectors;
- clustering the mean vectors;
- sampling input mean vectors from each cluster; and
- using an artificial intelligence model, comprising a plurality of weights, convert each sampled input mean vectors to a patch-level score.

13. The system of claim 12, wherein the region of interest and outcome prediction module is further configured to perform steps comprising:
- selecting a first group of patches having highest patch-level scores amongst the patch-level scores;
- selecting a second group of patches having lowest patch-level scores amongst the path-level scores;
- combining the first and second groups; and
- generating the patient-level score.

14. The system of claim 13, wherein the region of interest and outcome prediction module is further configured to perform steps comprising:
- comparing the patient-level score for a patient to the patient outcome data; and
- if the patient-level score does not align with the patient outcome data modify the weights of the artificial intelligence model.

15. The system of claim 11, wherein the region of interest and outcome prediction module is further configured to identify regions of interest in the patient tissue image slide, at least partly based on the patch-level scores, wherein the regions of interest comprise biomarkers predictive of patient outcome.

16. The system of claim 15 further comprising of a spatial profiling and biomarker identification module configured to:
- perform molecular analysis on the regions of interest; and
- identify biomarkers based at least partly on differential expressions of one or of DNA, RNA or proteins on the regions of interest versus other regions of the patient tissue image slide, wherein the biomarkers are over- or under-expressed in the regions of interest versus other regions, wherein molecular analysis reveals biologically discrete subsets and pathways and mechanism-related response and outcome.

17. The system of claim 15 further comprising a co-registration module configured to:
- generate a biomarker slide based on the identified biomarkers;
- generate a patient tissue image slide annotated with the regions of interest; and
- superimpose the biomarker slide and the annotated patient tissue image slide.

18. The system of claim 11, wherein the disease detection and grading module is further configured to generate labeled patch vectors by:
- receiving a plurality of auxiliary labels; and
- when an auxiliary label is applicable to a patch vector or its corresponding patch, determine the label of the patch by processing the patch through the artificial intelligence network at a plurality of distinct sizes and/or resolutions.

19. The system of claim 11, wherein the disease detection and grading module is further configured to:
- cluster the input training data of the artificial intelligence network based, at least partly, on the output vectors of the artificial intelligence network, wherein the output vectors of the artificial intelligence network indicate an underlying morphological pattern in the patient image slide; and
- sample uniformly across the clusters of the input training data in subsequent training passes of the artificial intelligence network.

20. The system of claim 11, wherein the disease detection and grading module is further configured to:
- assign labels to patch vectors based, at least partly, on a confidence level;
- determine label assignments having a low confidence level;
- determine input patch vectors generating the low confidence level assignments; and
- sample input training data of the artificial intelligence network to include a pre-determined percentage of input training data from the input patch vectors having generated low confidence level assignments in previous training passes of the artificial intelligence network.

\* \* \* \* \*